United States Patent [19]
Vinkemeier et al.

[11] Patent Number: 6,030,780
[45] Date of Patent: Feb. 29, 2000

[54] PURIFIED STAT PROTEINS AND METHODS OF PURIFYING THEREOF

[75] Inventors: Uwe Vinkemeier, New York; James E. Darnell, Jr., Larchmont, both of N.Y.

[73] Assignee: The Rockefeller University, New York, N.Y.

[21] Appl. No.: 08/951,130

[22] Filed: Oct. 15, 1997

Related U.S. Application Data

[60] Provisional application No. 60/028,176, Oct. 15, 1996.

[51] Int. Cl.[7] .............................. C12Q 1/68; G01N 33/53
[52] U.S. Cl. ................................................. 435/6; 435/7.1
[58] Field of Search .................................. 435/69.1, 91.1, 435/177.1, 7.1, 94, 501, 4, 6; 424/185.1; 514/2, 44; 536/23.1, 24.5, 24.11, 23.5

[56] References Cited

U.S. PATENT DOCUMENTS

| | | | |
|---|---|---|---|
| 5,322,801 | 6/1994 | Kingston et al. | 436/5.01 |
| 5,543,304 | 8/1996 | Mulks et al. | 435/69.3 |
| 5,607,833 | 3/1997 | Gilman et al. | 435/6 |
| 5,648,217 | 7/1997 | Levy | 435/6 |
| 5,710,266 | 1/1998 | McKnight et al. | 536/23.5 |
| 5,716,622 | 2/1998 | Darnell et al. | 424/185.1 |
| 5,821,053 | 10/1998 | Auron et al. | 436/6 |

FOREIGN PATENT DOCUMENTS

| | | |
|---|---|---|
| WO 93/19179 | 9/1993 | WIPO . |
| WO 95/08629 | 3/1995 | WIPO . |

OTHER PUBLICATIONS

Zhong et al. Proc. Nat'l. Acad. Sci. U.S.A. vol. 91, pp. 4806–4810, May 1994.
Xu et al. Science. vol. 273, pp. 794–796, Sep. 1996.
Bergad et al. (1995) J. Biol. Chem. 270:24903–10.
Darnell et al., 1994, Science 264, 1415–1421.
Fried et al., 1992, Nucl. Acids Res. 9, 6505–6525.
Guyer et al., 1995, J. Immunol. 155, 3472–3480.
Horvath et al., 1995, Genes & Devel. 9, 984–994.
Ihle, 1995, Nature 377, 591–594.
Leung et al., 1996, Science 273 750–751.
Levy et al., 1989, Genes & Devel. 3, 1362–1372.
Muller et al., 1993, EMBO J 12, 4221–4228.
Qureshi et al., 1995, Proc. Natl. Acad. Sci. USA 92, 3829–3833.
Schindler and Darnell, 1995, Annu. Rev. Biochem. 64, 621–51.
Schindler et al., 1992, Proc. Natl. Acad. Sci. USA 89, 7836–7839.
Shuai et al., 1994, Cell 76, 821–828.
Shuai et al., 1993, Science 261, 1744–1746.
Shuai et al., 1993, Nature 366, 580–583.
Shuai et al., 1992, Science 259, 1808–1812.
Wagner et al., 1990, EMBO J. 9, 4477–4484.
Wen et al., 1995, Cell 82, 241–250.
Yan et al., 1995, Nucl. Acids Res. 23, 459–463.
Yan R., et al., 1996, Cell 84, 421–430.

*Primary Examiner*—James Ketter
*Assistant Examiner*—Irem Yucel
*Attorney, Agent, or Firm*—Klauber & Jackson

[57] ABSTRACT

The present invention describes methods of producing milligram quantities of three forms of purified Stat1 protein from recombinant DNA constructs. In addition, the Stat proteins may be isolated in their phosphorylated or non-phosphorylated forms (Tyr 701). The proteins can be produced in baculovirus infected insect cells, or *E. coli*. A compact domain in the amino terminus of Stat1α was isolated and found to enhance DNA binding due to its ability to interact with a neighboring Stat protein. A relatively protease-resistant recombinant truncated form of the Stat protein was isolated in 40–50 mg quantities. Purification of the Stat proteins were performed after modifying specific cysteine residues of the Stat proteins to prevent aggregation. Activated EGF-receptor partially purified from membranes by immunoprecipitation was shown to be capable of in vitro catalysis of the phosphorylation of the tyrosine residue of Stat1 known to be phosphorylated in vivo. Techniques are enclosed to separate the phosphorylated from the nonphosphorylated Stat proteins. The techniques disclosed are general for Stat proteins and may be used to isolate large quantities of purified Stat 2, 3, 4, 5A, 5B and 6. Methods for using purified Stat proteins, truncated Stat proteins, or Stat N-terminal fragments for drug discovery are also disclosed.

7 Claims, 15 Drawing Sheets

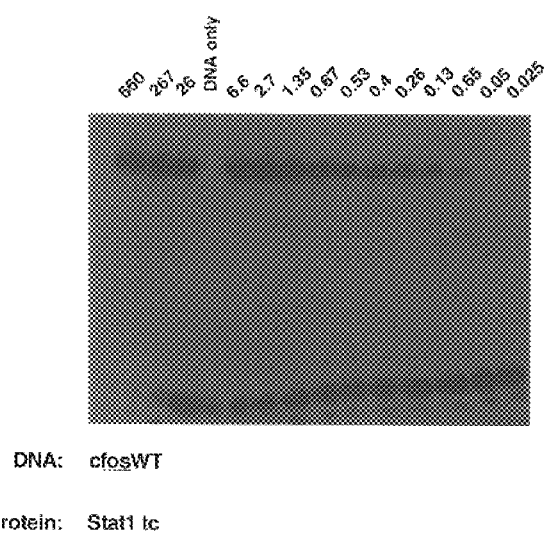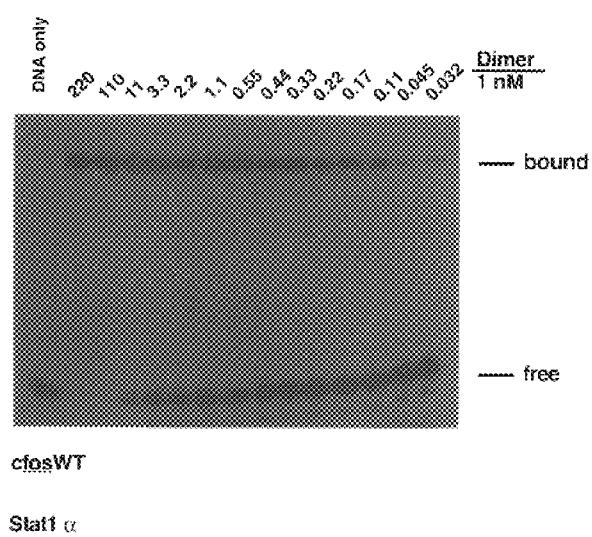

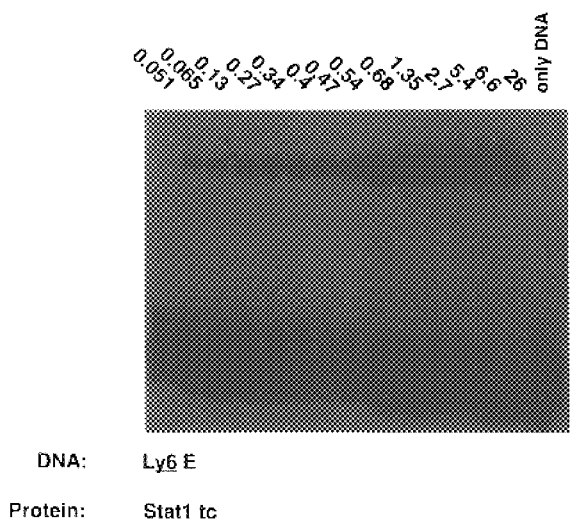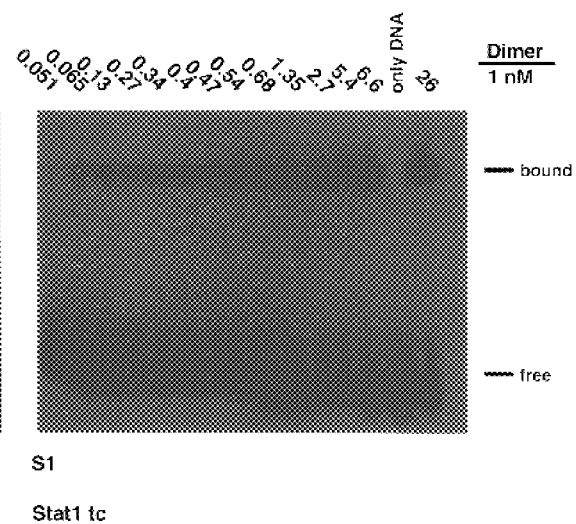

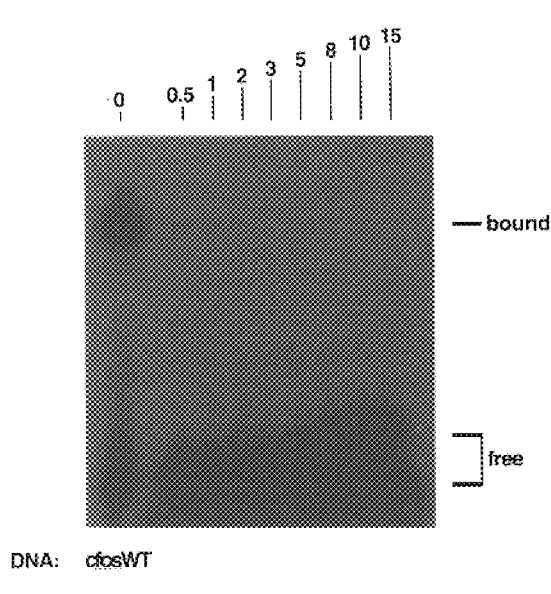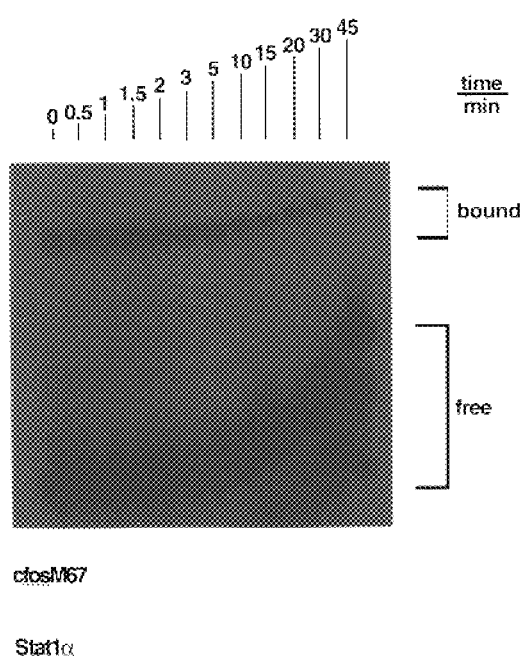

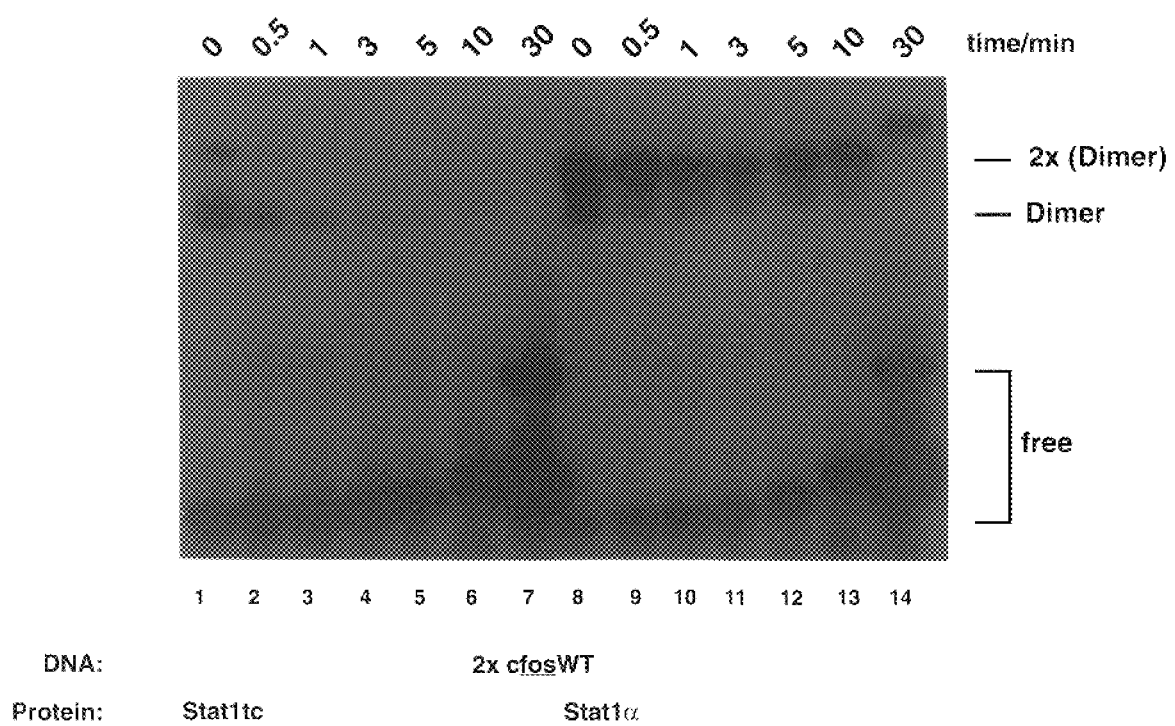

SEQUENCE LISTING

<160> NUMBER OF SEQ ID NOS: 16

<210> SEQ ID NO 1
<211> LENGTH: 750
<212> TYPE: PRT
<213> ORGANISM: Homo sapiens

<400> SEQUENCE: 1

Met Ser Gln Trp Tyr Glu Leu Gln Gln Leu Asp Ser Lys Phe Leu Glu
 1               5                   10                  15

-continued

```
Gln Val His Gln Leu Tyr Asp Asp Ser Phe Pro Met Glu Ile Arg Gln
             20                  25                  30

Tyr Leu Ala Gln Trp Leu Glu Lys Gln Asp Trp Glu His Ala Ala Asn
             35                  40                  45

Asp Val Ser Phe Ala Thr Ile Arg Phe His Asp Leu Leu Ser Gln Leu
             50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
             100                 105                 110

Arg Lys Ile Leu Glu Asn Ala Gln Arg Phe Asn Gln Ala Gln Ser Gly
             115                 120                 125

Asn Ile Gln Ser Thr Val Met Leu Asp Lys Gln Lys Glu Leu Asp Ser
             130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                 165                 170                 175

Leu Gln Asn Arg Glu His Glu Thr Asn Gly Val Ala Lys Ser Asp Gln
             180                 185                 190

Lys Gln Glu Gln Leu Leu Leu Lys Lys Met Tyr Leu Met Leu Asp Asn
             195                 200                 205

Lys Arg Lys Glu Val Val His Lys Ile Ile Glu Leu Leu Asn Val Thr
             210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                 245                 250                 255

Asp Gln Leu Gln Asn Trp Phe Thr Ile Val Ala Glu Ser Leu Gln Gln
             260                 265                 270

Val Arg Gln Gln Leu Lys Lys Leu Glu Glu Leu Glu Gln Lys Tyr Thr
             275                 280                 285

Tyr Glu His Asp Pro Ile Thr Lys Asn Lys Gln Val Leu Trp Asp Arg
             290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                 325                 330                 335

Thr Gly Val Gln Phe Thr Val Lys Leu Arg Leu Leu Val Lys Leu Gln
             340                 345                 350

Glu Leu Asn Tyr Asn Leu Lys Val Lys Val Leu Phe Asp Lys Asp Val
             355                 360                 365

Asn Glu Arg Asn Thr Val Lys Gly Phe Arg Lys Phe Asn Ile Leu Gly
             370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                 405                 410                 415

Thr Arg Thr Asn Glu Gly Pro Leu Ile Val Thr Glu Glu Leu His Ser
             420                 425                 430
```

-continued

```
Leu Ser Phe Glu Thr Gln Leu Cys Gln Pro Gly Leu Val Ile Asp Leu
        435                 440                 445

Glu Thr Thr Ser Leu Pro Val Val Ile Ser Asn Val Ser Gln Leu
        450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
                500                 505                 510

Gly Leu Asn Val Asp Gln Leu Asn Met Leu Gly Glu Lys Leu Leu Gly
        515                 520                 525

Pro Asn Ala Ser Pro Asp Gly Leu Ile Pro Trp Thr Arg Phe Cys Lys
        530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
                580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
        610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
        675                 680                 685

Glu Pro Met Glu Leu Asp Gly Pro Lys Gly Thr Gly Tyr Ile Lys Thr
        690                 695                 700

Glu Leu Ile Ser Val Ser Glu Val His Pro Ser Arg Leu Gln Thr Thr
705                 710                 715                 720

Asp Asn Leu Leu Pro Met Ser Pro Glu Glu Phe Asp Glu Val Ser Arg
                725                 730                 735

Ile Val Gly Ser Val Glu Phe Asp Ser Met Met Asn Thr Val
                740                 745                 750

<210> SEQ ID NO 2
<211> LENGTH: 712
<212> TYPE: PRT
<213> ORGANISM: Homo sapiens

<400> SEQUENCE: 2

Met Ser Gln Trp Tyr Glu Leu Gln Gln Leu Asp Ser Lys Phe Leu Glu
 1               5                  10                  15

Gln Val His Gln Leu Tyr Asp Asp Ser Phe Pro Met Glu Ile Arg Gln
                20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
        50                  55                  60
```

-continued

```
Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                 85                  90                  95

Asp Pro Ile Gln Met Ser Met Ile Ile Tyr Ser Cys Leu Lys Glu Glu
                100                 105                 110

Arg Lys Ile Leu Glu Asn Ala Gln Arg Phe Asn Gln Ala Gln Ser Gly
            115                 120                 125

Asn Ile Gln Ser Thr Val Met Leu Asp Lys Gln Lys Glu Leu Asp Ser
130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
                180                 185                 190

Lys Gln Glu Gln Leu Leu Leu Lys Lys Met Tyr Leu Met Leu Asp Asn
            195                 200                 205

Lys Arg Lys Glu Val Val His Lys Ile Ile Glu Leu Leu Asn Val Thr
210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
                260                 265                 270

Val Arg Gln Gln Leu Lys Lys Leu Glu Glu Leu Glu Gln Lys Tyr Thr
            275                 280                 285

Tyr Glu His Asp Pro Ile Thr Lys Asn Lys Gln Val Leu Trp Asp Arg
            290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
                340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
            370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
            450                 455                 460

Pro Ser Gly Trp Ala Ser Ile Leu Trp Tyr Asn Met Leu Val Ala Glu
465                 470                 475                 480
```

```
Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
        530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
        610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
                675                 680                 685

Glu Pro Met Glu Leu Asp Gly Pro Lys Gly Thr Gly Tyr Ile Lys Thr
        690                 695                 700

Glu Leu Ile Ser Val Ser Glu Val
705                 710

<210> SEQ ID NO 3
<211> LENGTH: 582
<212> TYPE: PRT
<213> ORGANISM: Homo sapiens

<400> SEQUENCE: 3

Ser Thr Val Met Leu Asp Lys Gln Lys Glu Leu Asp Ser Lys Val Arg
  1               5                  10                  15

Asn Val Lys Asp Lys Val Met Cys Ile Glu His Glu Ile Lys Ser Leu
                 20                  25                  30

Glu Asp Leu Gln Asp Glu Tyr Asp Phe Lys Cys Lys Thr Leu Gln Asn
             35                  40                  45

Arg Glu His Glu Thr Asn Gly Val Ala Lys Ser Asp Gln Lys Gln Glu
         50                  55                  60

Gln Leu Leu Leu Lys Lys Met Tyr Leu Met Leu Asp Asn Lys Arg Lys
 65                  70                  75                  80

Glu Val Val His Lys Ile Ile Glu Leu Leu Asn Val Thr Glu Leu Thr
                 85                  90                  95

Gln Asn Ala Leu Ile Asn Asp Glu Leu Val Glu Trp Lys Arg Arg Gln
            100                 105                 110

Gln Ser Ala Cys Ile Gly Gly Pro Pro Asn Ala Cys Leu Asp Gln Leu
        115                 120                 125

Gln Asn Trp Phe Thr Ile Val Ala Glu Ser Leu Gln Gln Val Arg Gln
        130                 135                 140
```

-continued

```
Gln Leu Lys Lys Leu Glu Glu Leu Glu Gln Lys Tyr Thr Tyr Glu His
145                 150                 155                 160

Asp Pro Ile Thr Lys Asn Lys Gln Val Leu Trp Asp Arg Thr Phe Ser
            165                 170                 175

Leu Phe Gln Gln Leu Ile Gln Ser Ser Phe Val Val Glu Arg Gln Pro
            180                 185                 190

Cys Met Pro Thr His Pro Gln Arg Pro Leu Val Leu Lys Thr Gly Val
        195                 200                 205

Gln Phe Thr Val Lys Leu Arg Leu Leu Val Lys Leu Gln Glu Leu Asn
        210                 215                 220

Tyr Asn Leu Lys Val Lys Val Leu Phe Asp Lys Asp Val Asn Glu Arg
225                 230                 235                 240

Asn Thr Val Lys Gly Phe Arg Lys Phe Asn Ile Leu Gly Thr His Thr
                245                 250                 255

Lys Val Met Asn Met Glu Glu Ser Thr Asn Gly Ser Leu Ala Ala Glu
                260                 265                 270

Phe Arg His Leu Gln Leu Lys Glu Gln Lys Asn Ala Gly Thr Arg Thr
            275                 280                 285

Asn Glu Gly Pro Leu Ile Val Thr Glu Glu Leu His Ser Leu Ser Phe
290                 295                 300

Glu Thr Gln Leu Cys Gln Pro Gly Leu Val Ile Asp Leu Glu Thr Thr
305                 310                 315                 320

Ser Leu Pro Val Val Ile Ser Asn Val Ser Gln Leu Pro Ser Gly
                325                 330                 335

Trp Ala Ser Ile Leu Trp Tyr Asn Met Leu Val Ala Glu Pro Arg Asn
            340                 345                 350

Leu Ser Phe Phe Leu Thr Pro Pro Cys Ala Arg Trp Ala Gln Leu Ser
        355                 360                 365

Glu Val Leu Ser Trp Gln Phe Ser Ser Val Thr Lys Arg Gly Leu Asn
        370                 375                 380

Val Asp Gln Leu Asn Met Leu Gly Glu Lys Leu Leu Gly Pro Asn Ala
385                 390                 395                 400

Ser Pro Asp Gly Leu Ile Pro Trp Thr Arg Phe Cys Lys Glu Asn Ile
                405                 410                 415

Asn Asp Lys Asn Phe Pro Phe Trp Leu Trp Ile Glu Ser Ile Leu Glu
            420                 425                 430

Leu Ile Lys Lys His Leu Leu Pro Leu Trp Asn Asp Gly Cys Ile Met
        435                 440                 445

Gly Phe Ile Ser Lys Glu Arg Glu Arg Ala Leu Leu Lys Asp Gln Gln
450                 455                 460

Pro Gly Thr Phe Leu Leu Arg Phe Ser Glu Ser Ser Arg Glu Gly Ala
465                 470                 475                 480

Ile Thr Phe Thr Trp Val Glu Arg Ser Gln Asn Gly Gly Glu Pro Asp
                485                 490                 495

Phe His Ala Val Glu Pro Tyr Thr Lys Lys Glu Leu Ser Ala Val Thr
            500                 505                 510

Phe Pro Asp Ile Ile Arg Asn Tyr Lys Val Met Ala Ala Glu Asn Ile
        515                 520                 525

Pro Glu Asn Pro Leu Lys Tyr Leu Tyr Pro Asn Ile Asp Lys Asp His
530                 535                 540

Ala Phe Gly Lys Tyr Tyr Ser Arg Pro Lys Glu Ala Pro Glu Pro Met
545                 550                 555                 560
```

-continued

Glu Leu Asp Gly Pro Lys Gly Thr Gly Tyr Ile Lys Thr Leu Ile
            565                 570                 575
Ser Val Ser Glu Val His
            580

<210> SEQ ID NO 4
<211> LENGTH: 131
<212> TYPE: PRT
<213> ORGANISM: Homo sapiens

<400> SEQUENCE: 4

Met Ser Gln Trp Tyr Glu Leu Gln Gln Leu Asp Ser Lys Phe Leu Glu
  1               5                  10                  15
Gln Val His Gln Leu Tyr Asp Asp Ser Phe Pro Met Glu Ile Arg Gln
             20                  25                  30
Tyr Leu Ala Gln Trp Leu Glu Lys Gln Asp Trp Glu His Ala Ala Asn
         35                  40                  45
Asp Val Ser Phe Ala Thr Ile Arg Phe His Asp Leu Leu Ser Gln Leu
     50                  55                  60
Asp Asp Gln Tyr Ser Arg Phe Ser Leu Glu Asn Asn Phe Leu Leu Gln
 65                  70                  75                  80
His Asn Ile Arg Lys Ser Lys Arg Asn Leu Gln Asp Asn Phe Gln Glu
                 85                  90                  95
Asp Pro Ile Gln Met Ser Met Ile Ile Tyr Ser Cys Leu Lys Glu Glu
            100                 105                 110
Arg Lys Ile Leu Glu Asn Ala Gln Arg Phe Asn Gln Ala Gln Ser Gly
        115                 120                 125
Asn Ile Gln
    130

<210> SEQ ID NO 5
<211> LENGTH: 1746
<212> TYPE: DNA
<213> ORGANISM: Homo sapiens

<400> SEQUENCE: 5
agcacagtga tgttagacaa acagaaagag cttgacagta aagtcagaaa tgtgaaggac      60
aaggttatgt gtatagagca tgaaatcaag agcctggaag atttacaaga tgaatatgac     120
ttcaaatgca aaaccttgca gaacagaaa cacgagacca atggtgtggc aaagagtgat     180
cagaaacaag aacagctgtt actcaagaag atgtatttaa tgcttgacaa taagagaaag     240
gaagtagttc acaaaataat agagttgctg aatgtcactg aacttaccca gaatgccctg     300
attaatgatg aactagtgga gtggaagcgg agacagcaga gcgcctgtat tgggggggccg     360
cccaatgctt gcttggatca gctgcagaac tggttcacta gttgcggga gagtctgcag     420
caagttcggc agcagcttaa aaagttggag gaattggaac agaaatacac ctacgaacat     480
gaccctatca caaaaacaa acaagtgtta tgggaccgca ccttcagtct tttccagcag     540
ctcattcaga gctcgtttgt ggtggaaaga cagcccctgca tgccaacgca ccctcagagg     600
ccgctggtct tgaagacagg ggtccagttc actgtgaagt tgagactgtt ggtgaaattg     660
caagagctga attataattt gaaagtcaaa gtcttatttg ataaagatgt gaatgagaga     720
aatacagtaa aggatttag gaagttcaac attttgggca cgcacacaaa agtgatgaac     780
atggaggagt ccaccaatgg cagtctggcg gctgaatttc ggcacctgca attgaaagaa     840
cagaaaatg ctggcaccag aacgaatgag ggtcctctca tcgttactga agagcttcac     900

-continued

```
tcccttagtt ttgaaaccca attgtgccag cctggtttgg taattgacct cgagacgacc    960
tctctgcccg ttgtggtgat ctccaacgtc agccagctcc cgagcggttg ggcctccatc   1020
ctttggtaca acatgctggt ggcggaaccc aggaatctgt ccttcttcct gactccacca   1080
tgtgcacgat gggctcagct ttcagaagtg ctgagttggc agttttcttc tgtcaccaaa   1140
agaggtctca atgtggacca gctgaacatg ttgggagaga agcttcttgg tcctaacgcc   1200
agccccgatg gtctcattcc gtggacgagg ttttgtaagg aaaatataaa tgataaaaat   1260
tttcccttct ggctttggat tgaaagcatc ctagaactaa ttaaaaaaca cctgctccct   1320
ctctggaatg atgggtgcat catgggcttc atcagcaagg agcgagagcg tgccctgttg   1380
aaggaccagc agccggggac cttcctgctg cggttcagtg agagctcccg ggaaggggcc   1440
atcacattca catgggtgga gcggtcccag aacggaggcg aacctgactt ccatgcggtt   1500
gaaccctaca cgaagaaaga actttctgct gttactttcc ctgacatcat tcgcaattac   1560
aaagtcatgg ctgctgagaa tattcctgag aatccctga agtatctgta tccaaatatt   1620
gacaaagacc atgcctttgg aaagtattac tccaggccaa aggaagcacc agagccaatg   1680
gaacttgatg gccctaaagg aactggatat atcaagactg agttgatttc tgtgtctgaa   1740
gttcac                                                              1746
```

<210> SEQ ID NO 6
<211> LENGTH: 393
<212> TYPE: DNA
<213> ORGANISM: Homo sapiens

<400> SEQUENCE: 6

```
atgtctcagt ggtacgaact tcagcagctt gactcaaaat tcctggagca ggttcaccag     60
ctttatgatg acagttttcc catggaaatc agacagtacc tggcacagtg gttagaaaag    120
caagactggg agcacgctgc caatgatgtt tcatttgcca ccatccgttt tcatgacctc    180
ctgtcacagc tggatgatca atatagtcgc ttttctttgg agaataactt cttgctacag    240
cataacataa ggaaaagcaa gcgtaatctt caggataatt ttcaggaaga cccaatccag    300
atgtctatga tcatttacag ctgtctgaag gaagaaagga aaattctgga aaacgcccag    360
agatttaatc aggctcagtc ggggaatatt cag                                 393
```

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 7

```
gggaattcca tatgagcaca gtgatgttag acaaac                               36
```

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 8

```
cggatcctat tagtgaactt cagacacaga aatc                                 34
```

<210> SEQ ID NO 9
<211> LENGTH: 17

```
<212> TYPE: DNA
<213> ORGANISM: Artificial Sequence
<220> FEATURE:
<223> OTHER INFORMATION: Description of Artificial Sequence:primer

<400> SEQUENCE: 9
gtattcccgt caatgca                                                17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 10
gtattcctgt aagatct                                                17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 11
gatttcccgt aaatcat                                                17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 12
gttgttccgg gaaaagg                                                17
<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 13
agtcagttcc cgtcaatgca tcaggttccc gtcaatgcat                       40

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 14
agtcagttcc cgtcaatgag ttcccgtcaa tgca                             34

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence:primer

<400> SEQUENCE: 15
agtcagttcc cgtcaatgat cgctacagag ttcccgtcaa gca                   43
```

```
<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:primer

<400> SEQUENCE: 16
agtcatttcc cgtcaatgca tcagttgacg ggaaagtagt                              40
```

PURIFIED STAT PROTEINS AND METHODS OF PURIFYING THEREOF

CROSS-REFERENCE TO RELATED APPLICATIONS

The present Application is based upon provisional application U.S. Ser. No. 60/028,176, filed Oct. 15, 1996, the disclosure of which is hereby incorporated by reference in its entirety. Applicants claim the benefits of this Application under 35 U.S.C. § 119(e).

GOVERNMENTAL SUPPORT

The research leading to the present invention was supported, at least in part, by NIH Grant Nos. AI32489 and AI34420. Accordingly, the Government may have certain rights in the invention.

FIELD OF THE INVENTION

The present invention relates generally to methods of purifying recombinant Stat proteins, modified Stat proteins and functional fragments thereof. Included in the present invention are the purified proteins and fragments themselves. The present invention also relates to methods of separating phosphorylated species of these proteins and fragments from the nonphosphorylated forms. The present invention also relates to methods for using purified Stat proteins, truncated Stat proteins or N-terminal fragments of Stat proteins for drug discovery.

BACKGROUND OF THE INVENTION

Transcription factors play a major role in cellular function by inducing the transcription of specific mRNAs. Transcription factors, in turn, are controlled by distinct signalling molecules. One particular family of transcription factor consists of the Signal Transducers and Activators of Transcription (Stat) proteins. Presently, there are seven known mammalian Stat family members. The recent discovery of Drosophila and Dictyostelium discoideum Stat proteins suggest that Stat proteins have played an important role in signal transduction since the early stages of our evolution [Yan R. et al., *Cell* 84:421–430 (1996); Kawata et al., *Cell* 89:909 (1997)].

Stat proteins mediate the action of a large group of signalling molecules including the cytokines and growth factors (Darnell et al. WO 95/08629, 1995). One distinctive characteristic of the Stat proteins are their apparent lack of requirement for changes in second messenger, e.g., cAMP or $Ca^{++}$, concentrations. Another characteristic is that stat proteins are activated in the cell cytoplasm by phosphorylation on a single tyrosine (Darnell et al., 1994; Schindler and Darnell, 1995). The responsible kinases are either ligand-activated transmembrane receptors with intrinsic tyrosine kinase activity, such as EGF- or PDGF-receptors, or cytokine receptors that lack intrinsic kinase activity but have associated JAK kinases, such as those for interferons and interleukins (Ihle, 1995). When Stat proteins are phosphorylated, they form homo- or heterodimeric structures in which the phosphotyrosine of one partner binds to the SRC homology domain (SH2) of the other. The newly formed dimer then translocates to the nucleus, binds to a palindromic GAS sequence, thereby activating transcription (Shuai et al., 1994; Qureshi et al., 1995; Leung et al., 1996).

Stat proteins serve in the capacity as a direct messengers between the cytokine or growth factor receptor present on the cell surface, and the cell nucleus. However, since each cytokine and growth factor produce a specific cellular effect by activating a distinct set of genes, the means in which such a limited number of Stat proteins mediate this result remains a mystery. Indeed, at least thirty different ligand-receptor complexes signal the nucleus through the seven known mammalian Stat proteins [Darnell et al., *Science* 277:1630–1635 (1997)].

Clearly there is a need to further study the biochemistry of Stat proteins. Unfortunately current studies are seriously hampered due to the low quantities of purified protein available. Full-length cDNAs for all mammalian Stats have been cloned. In addition, certain Stat proteins have been expressed in baculovirus-infected insect cells using a His tag at the COOH-terminal end and then purified by Ni-affinity chromatography (Xu, X., et al., note 9 (1996). However, no one has reported the production of milligram quantities of activated Stat protein, nor more importantly, a purification process amenable to scaling up for such quantitative isolations.

To perform the biochemical studies necessary to understand the mechanism of the Stat-mediated signal transduction, and to configure assays useful for the detection of compounds that modulate Stat function, there remains an unfulfilled requirement for the production of large amounts of pure protein. Furthermore, there is a need for a means of specifically phosphorylating the correct tyrosine residue on a Stat protein and then separating the resulting phosphorylated Stat protein from the unphosphorylated form in quantitative yields. In addition, there is a need to produce large quantities of stable, soluble truncated Stat proteins that retain functional activities of the corresponding native Stat protein. Finally, there is a need to develop methods of isolating these functional truncated Stat proteins.

The citation of any reference herein should not be construed as an admission that such reference is available as "Prior Art" to the instant application.

SUMMARY OF THE INVENTION

The present invention describes recombinant human Stat proteins which are produced in insect cells infected with recombinant baculovirus. Stable truncated forms of these proteins produced in bacteria are also included in the present invention. The present invention also includes labeled recombinant human Stat proteins and truncated Stat proteins. One aspect of this invention includes the purification of large amounts of these recombinant proteins. These isolated Stat proteins can be isolated in either their activated form, i.e., having a phosphorylated tyrosine, or in the nonphosphorylated state, where the corresponding tyrosine residue is not phosphorylated. A related aspect to the invention details the protease sensitivity of Stat proteins and the important consequences of this particular property. The present invention exploits this property and describes a recombinant truncated Stat protein that can be expressed in a bacterial host in large quantities, as a soluble protein that can be readily purified by the teaching of the present invention. The phosphorylated and nonphosphorylated form of the truncated Stat protein can also be individually isolated.

The expression of the truncated protein in a soluble form overcomes earlier failures, where recombinant Stat proteins formed almost exclusively insoluble inclusion bodies. Other potentially active fragments of Stat proteins that contain the DNA binding domain, either form insoluble inclusion bodies or are themselves so susceptible to proteolysis that isolation of the large quantities necessary for biochemical studies are not practical. Thus the present invention teaches for the first time, a soluble recombinant truncated Stat protein, as well as methods of its expression and isolation.

Although the present invention includes all Stat proteins, when specific amino acid residues are identified by number, the number represents the sequential position of that amino acid in the amino acid sequence of Stat1α. Thus, the number denoted for a specified amino acid in Stat1β and Stat1tc, as used herein, is per its corresponding position in the amino acid sequence of Stat1α.

The present invention includes a truncated Stat protein that can be expressed as a soluble recombinant protein in a bacterial host cell. In preferred embodiments the bacterial host is $E.$ $coli$, and the soluble truncated Stat protein makes up at least 30% of the total recombinant truncated Stat protein produced. In a more preferred embodiment the soluble truncated Stat protein makes up at least 50% of the total recombinant truncated Stat protein produced. In one embodiment, the truncated Stat protein has an amino acid sequence substantially similar to SEQ ID NO:3. In another embodiment, the truncated Stat protein has an amino acid sequence of SEQ ID NO:3. In preferred embodiments, the truncated Stat protein is purified. In one variation of this type, the purified truncated Stat protein exhibits a single protein band on 7% SDS-PAGE, run under reducing conditions.

The Stat proteins, including the truncated Stat proteins of the present invention are activated when a tyrosine residue of the protein is phosphorylated. In a preferred embodiment of this type, the phosphorylated tyrosine is tyrosine 701 of the Stat1α amino acid sequence shown in SEQ ID NO:1.

In one embodiment, the purified truncated Stat protein is substantially or completely free of its phosphorylated form. In another embodiment, the purified truncated Stat protein is substantially or completed phosphorylated. In yet a third embodiment, the purified truncated Stat protein is a mixture of the nonphosphorylated and phosphorylated forms.

One embodiment of the present invention is a purified Stat protein that is either substantially or completely free of its corresponding phosphorylated, activated form or in the alternative, is essentially or entirely in the corresponding phosphorylated, activated form. One variation of this embodiment exhibits a single protein band on 7% SDS-PAGE, run under reducing conditions, and has an amino acid sequence substantially similar to SEQ ID NO:1. In another variation the purified Stat protein, exhibits a single protein band on 7% SDS-PAGE, run under reducing conditions, and has an amino acid sequence substantially similar to SEQ ID NO:2. Yet another variation also includes a purified Stat protein that exhibits a single protein band on 7% SDS-PAGE, run under reducing conditions and has an amino acid sequence of SEQ ID NO:1. In still another variation of this embodiment, the purified Stat protein exhibits a single protein band on 7% SDS-PAGE, run under reducing conditions, and has an amino acid sequence of SEQ ID NO:2.

The truncated Stat proteins and purified Stat proteins including the purified truncated Stat proteins of the present invention can have a converted cysteine. The converted cysteine can be of the form of a modified cysteine, such as a cysteine having a blocked thiol group or of an analogue of cysteine such as homocysteine; or of an amino acid replacement for cysteine. In preferred embodiments of this last type, the amino acid replacement for cysteine is an alternative polar neutral amino acid such as glycine, serine, threonine, tyrosine, asparagine, or glutamine. In more preferred embodiments of this type, the alternative polar neutral amino acid is a glycine, a serine, or a threonine. In preferred embodiments containing modified cysteines, the modified cysteine is as an alkylated cysteine, or a cysteine containing a mercurial, or the thiol is oxidized and forms a disulfide bond with a second thiol moiety.

The alkylated cysteines may be alkylated by a variety of alkylating agents including iodoacetate, sodium tetracyanate, 5,5/dithiobis(2-nitrobenzoic acid), 2,2/-dithiobis(5-nitropyridine) and N-ethyl maleimide (NEM). In preferred embodiments the alkylated cysteines are alkylated by N-ethyl maleimide.

The purified truncated Stat proteins and purified Stat proteins, including the purified truncated Stat proteins of the present invention, can also have more than one converted cysteine. In one embodiment of this type, the Stat protein is Stat1α or a fragment thereof and has three converted cysteines at Cysteine 155, Cysteine 440, and Cysteine 492 of the Stat1α amino acid sequence shown in SEQ ID NO:1. The three converted cysteines can take any form as listed above, including each cysteine taking an alternative form. In one such embodiment Cysteine 155 is alkylated, Cysteine 440 is substituted by homocysteine, and Cysteine 492 is substituted by a threonine. In a preferred embodiment, all three converted cysteines are alkylated cysteines. All of these Stat proteins and purified Stat proteins can be purified to exhibit one band on 7% SDS-PAGE, under reducing conditions in either their phosphorylated, activated state or in their corresponding nonphosphorylated form.

The present invention also includes purified Stat N-terminal peptide fragments. These peptide fragments consist of a protein domain that can be selectively cleaved by mild proteolysis with subtilisin or proteinase K. The N-terminal peptide fragments can form homodimers. As part of a Stat protein, the N-terminal domain serves to enhance the binding of two adjacent Stat dimers to a pair of closely aligned DNA binding sites, i.e., binding sites separated by approximately 10 to 15 base pairs. In a preferred embodiment, the N-terminal peptide fragment has an amino acid sequence substantially similar to that of SEQ ID NO:4. In a more preferred embodiment, the N-terminal peptide fragment has an amino acid sequence of SEQ ID NO:4.

The present invention, also includes antibodies to the truncated Stat protein, and the N-terminal peptide fragment of a Stat protein, as purified from recombinant sources or produced by chemical synthesis, and derivatives or analogs thereof, including fusion proteins. Such antibodies include but are not limited to polyclonal, monoclonal, chimeric, single chain, Fab fragments, and a Fab expression library. These antibodies may be labeled.

The present invention also includes nucleic acids comprising nucleotide sequences that encode a truncated Stat protein. In one embodiment the nucleic acid comprises a nucleotide sequence that encodes a truncated Stat protein having an amino acid sequence that is substantially similar to SEQ ID NO:3. In a related embodiment the nucleic acid comprises a nucleotide sequence that encodes a truncated Stat protein having the amino acid sequence of SEQ ID NO:3. In yet another embodiment the nucleic acid comprises a nucleotide sequence that is substantially similar to SEQ ID NO:5 and codes for the expression of a truncated Stat protein. In still another embodiment the nucleic acid contains a nucleotide sequence having the sequence of SEQ ID NO:5.

The present invention also includes nucleic acids that comprise a nucleotide sequence encoding an N-terminal fragment of a Stat protein. In one embodiment the nucleic acid comprises a nucleotide sequence that encodes a Stat N-terminal fragment having an amino acid sequence that is substantially similar to SEQ ID NO:4. In a related embodiment the nucleic acid comprises a nucleotide sequence that encodes a Stat N-terminal fragment having the amino acid sequence of SEQ ID NO:4. In yet another embodiment the nucleic acid comprises a nucleotide sequence that is substantially similar to SEQ ID NO:6 and codes for the expression of a Stat N-terminal fragment. In still another embodiment the nucleic acid contains a nucleotide sequence having the sequence of SEQ ID NO:6.

All of the nucleic acids of the present invention can also contain heterologous nucleotide sequences.

Methods of phosphorylating the Stat proteins in vitro, are also included in the present invention. In one embodiment the phosphorylation is performed with a preparation of EGF-receptor kinase. In preferred embodiments the EGF-receptor preparation is obtained from cell lysates and purified with the use of an anti-EGF-receptor antibody directed against the extracellular domain. In some such embodiments the resulting EGF-receptor antibody complex is precipitated with Protein A agarose beads. In another preferred embodiment the antibody is a monoclonal antibody. In yet another preferred embodiment the cell lysates are from humans. In the most preferred embodiment of this method, the antibody is a monoclonal antibody and the cell lysates are from humans.

The present invention also includes methods of separating phosphorylated Stat proteins including phosphorylated truncated Stat proteins from their nonphosphorylated counterparts. Although these methods may be properly applied to all Stat proteins, and their corresponding truncated proteins, in preferred embodiments the Stat protein has an amino acid sequence of SEQ ID NO:1 or SEQ ID NO:2, and the truncated Stat protein has an amino acid sequence substantially similar to SEQ ID NO:3. In more preferred embodiments the Stat protein or the truncated Stat protein also has a converted cysteine. In the most preferred embodiment, the Stat protein or truncated Stat protein has three converted cysteines which are alkylated cysteines at Cysteine 155, Cysteine 440, and Cysteine 492 of the Stat1α amino acid sequence shown in SEQ ID NO:1.

In one embodiment a mixture containing phosphorylated Stat protein and nonphosphorylated Stat protein are placed onto a heparin-solid support. In preferred embodiments the heparin solid support is either heparin agarose, heparin SEPHADEX or heparin cellulose. In the most preferred embodiment the heparin-solid support is heparin agarose.

In one variation of this embodiment the heparin agarose is washed first with a low-salt buffer to remove materials that either bind more weakly than the nonphosphorylated Stat protein or do not bind at all. The Stat proteins are eluted from the heparin agarose as a function of salt concentration with the nonphosphorylated Stat protein eluting at a lower salt concentration than the phosphorylated protein. In one particular embodiment of this type, the protein is eluted with a salt gradient. In a preferred embodiment, the elution of the heparin agarose is performed stepwise with an approximately 0.15 M monovalent salt elution step, followed by an approximately 0.4 M monovalent salt elution step. In this case the unphosphorylated Stat protein elutes during the first elution step, and the phosphorylated Stat protein elutes during the second elution step. In a more preferred embodiment the monovalent salt is potassium chloride.

This procedure may be performed by a batchwise method, though in preferred embodiments the heparin agarose is placed in a column. The procedure may be performed by simple controlled pumping of the column, or by HPLC, FPLC and any other analogous methodology; or the column may be allowed to flow by the pressure of gravity.

The present invention also includes methods of preparing a purified alkylated Stat protein and methods of preparing a purified alkylated truncated Stat protein. Although these methods may be properly applied to all Stat and truncated Stat proteins, in preferred embodiments the Stat protein has an amino acid sequence of SEQ ID NO:1 or SEQ ID NO:2, and the truncated Stat protein has an amino acid sequence substantially similar to SEQ ID NO:3. In one such embodiment an expression vector containing a nucleic acid that encodes a Stat protein is placed into a compatible host cell, and the Stat protein is expressed. The compatible host cell is grown, harvested and then the expressed Stat protein is released from the host cell. In a preferred embodiment the expressed Stat protein is released from the host cell by lysing the cells. The Stat protein is then treated with an alkylating agent to alkylate one or more cysteines involved in intersubunit aggregation. The alkylated Stat protein is then isolated, yielding a purified alkylated Stat protein.

In another such embodiment, the expression vector contains a nucleic acid that encodes a truncated Stat protein. The truncated Stat protein has an amino acid sequence having an N-terminal sequence that is substantially similar to the N-terminus of the corresponding resulting Stat protein following the cleavage of the proteolytic sensitive N-terminal domain from the corresponding Stat protein. The carboxyl terminus of the truncated Stat protein extends at least to the phosphorylatable tyrosine required for homodimerization. In preferred embodiments, alkylation is performed by incubating the Stat protein with N-ethyl maleimide. In more preferred embodiments, about 40 to 50 mg of purified alkylated truncated Stat protein can be obtained from 6 liters of starting culture. These methods can also include a step of phosphorylating the Stat protein either prior to or preferably following alkylation. In preferred methods of this type, preparations of EGF-receptor kinase are used in the in vitro phosphorylating step.

The present invention also includes methods of preparing a purified substituted Stat protein including methods of preparing a purified substituted truncated Stat protein. Although these methods may be properly applied to all Stat proteins including truncated Stat proteins, in preferred embodiments the Stat protein has an amino acid sequence of SEQ ID NO:1 or SEQ ID NO:2, and the truncated Stat protein has an amino acid sequence substantially similar to SEQ ID NO:3. In one such embodiment, an expression vector contains a nucleic acid that encodes a substituted Stat protein that has an alternative amino acid substituted for a cysteine of the Stat protein, thereby replacing it. In one preferred embodiment, the amino acid is a polar neutral amino acid. In a variation of this embodiment the alternative polar neutral amino acid is a glycine. In another variation of this embodiment, the alternative polar neutral amino acid is a serine. In still another variation of this embodiment, the alternative polar neutral amino acid is a threonine. In preferred embodiments, the cysteine that has been replaced was involved in the intersubunit aggregation that takes place between Stat proteins.

The expression vector is then placed into a compatible host cell, and the substituted Stat protein is expressed. The compatible host cell is grown, harvested and then the expressed substituted Stat protein is released from the host cell. In a preferred embodiment the expressed Stat protein is released from the host cell by lysing the cells. The substituted Stat protein is then isolated, yielding a purified substituted Stat protein.

In one embodiment, the expression vector contains a nucleic acid that encodes a substituted truncated Stat protein. In one such embodiment, an expression vector contains a nucleic acid that encodes a substituted truncated Stat protein that has an alternative polar neutral amino acid substituted for a cysteine of the Stat protein, thereby replacing it. In one variation of this embodiment, the alternative polar neutral amino acid is a glycine. In another variation of this embodiment, the alternative polar neutral amino acid is a serine. In yet another variation of this embodiment, the alternative polar neutral amino acid is a threonine. In a preferred embodiment, the cysteine that has been replaced was involved in the intersubunit aggregation that takes place between Stat proteins. The substituted truncated Stat protein has an amino acid sequence which is essentially the same as the protease-resistant domain of the Stat protein. In preferred embodiments, about 40 to 50 mg of purified substituted truncated Stat protein can be obtained from 6 liters of starting culture. These methods can also include a step of phosphorylating the Stat protein or truncated Stat protein. In a preferred methods of this type, an EGF-receptor kinase preparation is used in the in vitro phosphorylating step.

In some embodiments, a substituted Stat protein or a substituted truncated Stat protein is also alkylated. In such cases an expression vector containing a nucleic acid that encodes a substituted Stat protein or a substituted truncated Stat protein is placed into a compatible host cell, and expressed. In one embodiment the substituted Stat protein contains a replacement amino acid that is an alternative polar neutral amino acid. In a preferred embodiment the alternative polar neutral amino acid is a glycine, a serine, or a threonine. The compatible host cell is grown, harvested and then the expressed substituted Stat protein or substituted truncated Stat protein is released from the host cell as described herein. The substituted Stat protein or substituted truncated Stat protein is then treated with an alkylating agent to alkylate one or more cysteines involved in intersubunit aggregation. The alkylated substituted Stat protein or alkylated substituted truncated Stat protein is then isolated, yielding a purified alkylated substituted Stat protein or purified alkylated substituted truncated Stat protein. In preferred embodiments, alkylation is performed by incubating the Stat protein or truncated Stat protein with N-ethyl maleimide. In more preferred embodiments about 40 to 50 mg of purified alkylated substituted truncated Stat protein can be obtained from 6 liters of starting culture.

The present invention also includes methods of identifying drugs that effect the interaction of N-terminal domains of Stat proteins that are bound to adjacent DNA binding sites. In one such embodiment, a drug library is screened by assaying the binding activity of a Stat protein to its DNA binding site. This assay is based on the ability of the N-terminal domain of Stat proteins to substantially enhance the binding affinity of two adjacent Stat dimers to a pair of closely aligned DNA binding sites, i.e., binding sites separated by approximately 10 to 15 base pairs. Such drug libraries include phage libraries as described below, chemical libraries compiled by the major drug manufacturers, mixed libraries, and the like. Any of such compounds contained in the drug libraries are suitable for testing as a prospective drug in the assays described below, and further in a high throughput assay based on the methods described below.

One such embodiment includes a method of identifying a drug that interferes with the interaction of the N-terminal domains of Stat proteins bound to DNA binding sites. One variation of this embodiment relies on a truncated Stat protein that is missing the N-terminal domain responsible for enhancing the binding of two adjacent Stat dimers to a pair of closely aligned DNA binding sites. The binding affinity of a Stat protein to a DNA binding site effected by the N-terminal interaction of Stat proteins is determined. The effect of a prospective drug on the affinity of the Stat protein-DNA binding is determined. If the prospective drug decreases the binding affinity of the Stat protein to a DNA binding site, it becomes a candidate drug. The binding affinity of the corresponding truncated Stat protein to that DNA binding site is also determined. The effect of a candidate drug on the affinity of the truncated Stat protein-DNA binding is determined. If the candidate drug has no effect on the truncated Stat protein-DNA binding, then it can be concluded that the candidate drug interferes with the interaction of N-terminal domains of Stat proteins bound to adjacent DNA binding sites. In a preferred embodiment, the truncated Stat protein has an amino acid sequence that is substantially similar to SEQ ID NO:3.

This variation also includes a method of identifying a drug that enhances the interaction of the N-terminal domains of Stat proteins bound to DNA binding sites. The binding affinity of a Stat protein to a DNA binding site effected by the N-terminal interaction of Stat proteins is determined. The effect of a prospective drug on the affinity of the Stat protein-DNA binding is determined. If the prospective drug increases the binding affinity of the Stat protein to a DNA binding site, it becomes a candidate drug. The binding affinity of the corresponding truncated Stat protein to that DNA binding site is also determined. The effect of a candidate drug on the affinity of the truncated Stat protein-DNA binding is determined. If the candidate drug has no effect on the truncated Stat protein-DNA binding, then it can be concluded that the candidate drug enhances the interaction of N-terminal domains of Stat proteins bound to adjacent DNA binding sites. In a preferred embodiment, the truncated Stat protein has an amino acid sequence that is substantially similar to SEQ ID NO:3.

In another embodiment, a drug library is screened by assaying the binding activity of the two N-terminal fragments of the present invention. As disclosed in the present invention, the N-terminal fragments of Stat proteins form stable dimers in solution. These dimers could mimic the role the N-terminal domain plays in the native Stat protein. Therefore, a prospective drug capable of disrupting or enhancing the stability of the dimer formed between two N-terminal fragments becomes a candidate for a drug capable of destabilizing or stabilizing respectively, N-terminal domain-dependent Stat-DNA binding. These candidate drugs then can be tested in an in vitro or in vivo assay with Stat proteins. For example, dimerization of the N-terminal fragments in solution can be determined using techniques such as fluorescence depolarization.

In yet another embodiment, an N-terminal fragment of a Stat protein is attached to a solid support. The solid support is washed to remove unreacted species. A solution of free N-terminal fragments is poured onto the solid support and the N-terminal fragments are allowed to form dimers with their bound counterparts. In one variation, the solid support is washed again to remove N-terminal fragments that do not bind. Prospective drugs can be screened for their ability to disrupt the dimers, or the formation of the dimers, and thereby increase the concentration of free N-terminal fragments. In a variation of this embodiment, prospective drugs may be screened that enhance the binding of the free N-terminal fragments with their bound counterparts. In this case, there is a corresponding decrease in the concentration free N-terminal fragments. In either case, the measurement of an equilibrium constant, or a dissociation rate constant or an off-rate, may be used to express the effect of the prospective drug on the N-terminal fragment dimer binding. In another variation of this embodiment, prospective drugs that modulate the interaction of the N-terminal domain can be screened by determining the amount of N-terminal fragment that remains bound in the presence of the prospective drug. As compared to the amount of bound fragment in the absence of a prospective drug, prospective drugs that disrupt the interaction result in lower levels of bound fragments, whereas prospective drugs which enhance the interaction result in higher levels of bound fragment. One method of monitoring such interactions is through the use of free N-terminal fragments which have been labeled. Some suitable labels are exemplified below. Alternatively, the dimerization of the free N-terminal fragments with the bound N-terminal fragments can be monitored by changes in surface plasmon resonance. In preferred embodiments the N-terminal fragment has an amino acid sequence substantially similar to SEQ ID NO:4.

In yet another embodiment, the affect of a prospective drug (a test compound) on interactions between N-terminal domains of STATs is assayed in living cells that contain or can be induced to contain activated STAT proteins, i.e., STAT protein dimers. Cells containing a reporter gene, such as the heterologous gene for luciferase, green fluorescent protein, chloramphenicol acetyl transferase or β-galactosidase, operably linked to a promoter comprising two weak STAT binding sites are contacted with a prospective drug in the presence of a cytokine which activates the STAT(s) of interest. The amount (and/or activity) of reporter produced in the absence and presence of prospective drug is determined and compared. Prospective drugs which reduce the amount (and/or activity) of reporter produced are candidate antagonists of the N-terminal interaction, whereas prospective drugs which increase the amount (and/or activity) of reporter produced are candidate agonists. Cells containing a reporter gene operably linked to a promoter comprising strong STAT binding sites are then contacted with these candidate drugs, in the presence of a cytokine which activates the STAT(s) of interest. The amount (and/or activity) of reporter produced in the presence and absence of candidate drugs is determined and compared. Drugs which disrupt interactions between the N-terminal domains of the STATs will not reduce reporter activity in this second step. Similarly, candidate drugs which enhance interactions between N-terminal domains of STATs will not increase reporter activity in this second step.

In an analogous embodiment, two reporter genes each operably under the control of one of the two types promoters described above can be comprised in a single host cell as long as the expression of the two reporter gene products can be distinguished. For example, different modified forms of green fluorescent protein can be used as described in U.S. Pat. No. 5,625,048, Issued Apr. 29, 1997, hereby incorporated by reference in its entirety.

Antagonists of the STAT N-terminal interaction would be expected to antagonize aspects of STAT function. Such candidate drugs are expected to be useful for the treatment of a variety of disease states, including but not limited to, inflammation, allergy, asthma, and leukemias. Candidate drugs which stabilize the N-terminal interaction would be expected to enhance STAT function, and may therefore have utility in the treatment of anemias, neutropenias, thrombocytopenia, cancer, obesity, viral diseases and growth retardation, or other diseases characterized by a insufficient STAT activity.

These and other aspects of the present invention will be better appreciated by reference to the following drawings and Detailed Description.

BRIEF DESCRIPTION OF THE DRAWINGS

FIG. 4A and 4B Titration of $^{32}$P labelled cfosWT oligonucleotide with phosphorylated Stat1tc and full length Stat1α. A fixed amount of $^{32}$P labelled cfosWT oligonucleotide ($5.6 \times 10^{-10}$ M) was incubated with Stat1 proteins in a 12.5 µl volume as described in Materials and Methods. Numbers above the lanes indicate the concentrations of dimeric Stat1α and Stat1tc in each reaction. Protein-bound (bound) and free (free) DNA is identified. The concentration of free protein dimers at half saturation was determined to be approximately 1 nM in both cases which corresponds to the apparent equilibrium constant $K_{eq}$. In the lanes marked above "DNA only" no Stat protein was included in the reaction.

FIGS. 5A and 5B Titration of phosphorylated truncated Stat1 protein with $^{32}$P labelled oligonucleotides containing a "low" (Ly6 E, left panel) or "high" (S1, right panel) affinity binding site. The DNA concentration was fixed at $2.6 \times 10^{-10}$ M and titrated in a 12.5 µl volume against a standard protein dilution series ranging from $5 \times 10^{-11}$ M to $2.6 \times 10^{-8}$ M dimer final. Protein concentrations for the dimeric protein are given above each lane. The products were resolved on a native 4.5% polyacrylamide gel and quantified as described in experimental procedures. (Bound) protein/DNA complex; (free) free DNA. There was no Stat1tc included in reactions run on lanes denoted "only DNA". The dimer concentration at half saturation was determined from this autoradiograph to be approximately $1 \times 10^{-9}$ M for both DNA sequences.

FIGS. 5C and 5D The complex of Stat1α with cfosWT DNA is less stable than the complex with cfosM67 DNA. Results are shown for experiments designed to determine the off-rate in which $0.55 \times 10^{-9}$ M dimer was prebound with the radiolabelled DNA fragments (at $2 \times 10^{-9}$ M) containing the cfosWT (0 min; left panel) or cfosM67 (0 min; right panel) sequences. Excess unlabelled DNA (100×molar excess) was added to the reaction at time zero, and aliquots were taken at the indicated intervals and loaded onto a running gel to visualize the amount of complex remaining. The half life of the Stat1α/cfosWT complex is less than 0.5 min and that for the Stat1tc/cfosM67 complex in this titration is about 3 min. Because the electrophoresis was continuous during the experiment the DNA fragments (free) and the complexes (bound) are located progressively higher on the gel with increasing time, because the later samples were electrophoresed for shorter periods of time than were the earlier ones.

FIG. 6A. Comparison of the dissociation rates of complexes containing DNA fragments with two consecutive binding sites (2× cfosWT, 10 bp apart) and Stat1α (right) or Stat1tc (left). $0.5 \times 10^{-9}$ M dimer was prebound with $0.7 \times 10^{-9}$ M radiolabelled DNA for 5 min at room temperature (lanes 1 and 8). After the addition of a 100-fold molar excess of unlabelled DNA at time point zero the reaction was further incubated for the times indicated before aliquots were loaded on a running polyacrylamide gel. At time zero two differently migrating complexes are visible, denoted "(2×(Dimer))" and "Dimer". Unbound (free) DNA runs at the bottom of the gel.

DETAILED DESCRIPTION OF THE INVENTION

Figure 1A:
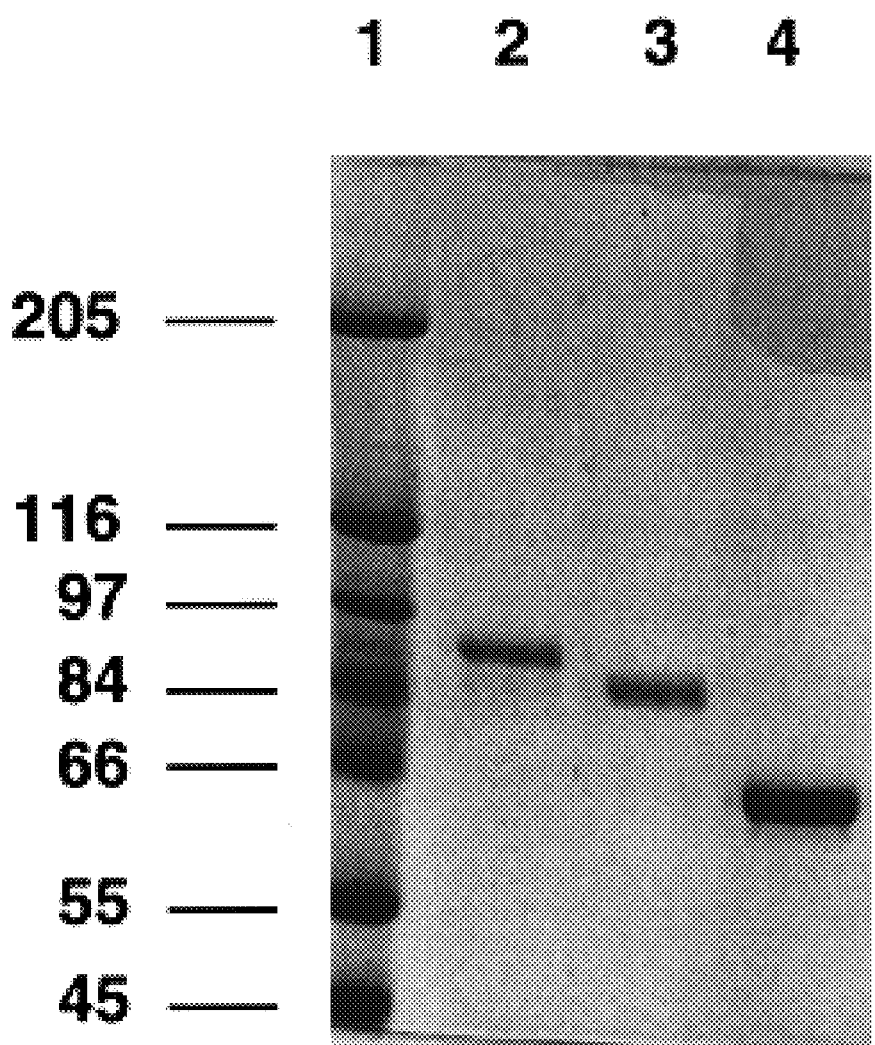
FIG. 1A. Polyacrylamide gel electrophoretic analysis of the purified nonphosphorylated proteins. Aliquots of Stat1α (lane 2; 2 μg), Stat1β (lane 3; 2 μg), and Stat1tc (lane 4; 4 μg) were run on a 7% SDS-PAGE gel and stained with Coomassie blue. Molecular weight standards were run in lane 1. $M_r$ is given as the kDa on the left.

The present invention includes methods for producing milligram quantities of different forms of purified Stat proteins from recombinant DNA constructs. One key aspect of the present invention is the isolation of purified phosphorylated Stat proteins. Another key aspect of the methods of the present invention comprises the modification of specific cysteine residues of the Stat proteins that prevent aggregation. In one preferred embodiment, the modification of the cysteine residues is performed by alkylation.

The present invention also includes a stable, soluble truncated Stat protein that retains most of the functional activities of the corresponding native Stat protein. Since a significant portion of the recombinant truncated Stat protein does not form inclusion bodies and therefore can be isolated in large quantities (40–50 mg of purified alkylated truncated Stat1 protein can be obtained from 6 liters of starting culture,) it is an excellent source of protein for the critical in vitro studies necessary to understand and later, control the signal transducing properties of Stat proteins. Nucleic acids that encode for a truncated Stat protein are also a part of the present invention. The present invention also includes methods of using the truncated Stat proteins for identifying drugs that specifically effect the interaction of N-terminal domains of Stat proteins that are bound to adjacent DNA binding sites.

The present invention includes the identification and isolation of an N-terminal fragment comprised of a compact domain in the amino terminus of Stat1α. This compact domain enhances the DNA binding of the Stat protein due to its ability to interact with a neighboring Stat protein. Methods of using this N-terminal fragment to identify specific drugs that act to either prevent or enhance the DNA binding of Stat proteins through interfering with or promoting the inter-protein interaction of the N-terminal domain of Stat proteins are also included.

The present invention also includes methods of phosphorylating, in vitro, the tyrosine residue of Stat proteins, known in vivo to cause the dimerization of the Stat protein upon being phosphorylated. In one preferred embodiment, activated EGF-receptor partially purified from membranes by immunoprecipitation is used to catalyze this phosphorylation.

In addition, the present invention includes methods of separating a phosphorylated Stat protein from its corresponding nonphosphorylated form. Heretofore, such separation could not be achieved due to the unusual behavior of Stat proteins on gel filtration columns.

Therefore, if appearing herein, the following terms shall have the definitions set out below.

As used herein a "converted cysteine" implies that a cysteine residue of a Stat protein or truncated Stat protein of the present invention has either been modified or replaced by an alternative naturally occurring or synthetic amino acid. A converted cysteine can be of the form of a modified cysteine such as a cysteine having its thiol group blocked, an analogue of cysteine such as homocysteine, or an amino acid replacement for cysteine such as a glycine or a serine. Modification of the modified cysteines can be accomplished through alkylation (i.e., forming an alkylated cysteine), or by mercuration, or through disulfide bond formation.

As used herein a the term "Stat protein" includes a particular family of transcription factor consisting of the Signal Transducers and Activators of Transcription proteins. These proteins have been defined in International Patent Publication No.s WO 93/19179 (Sep. 30, 1993, by James E. Darnell, Jr. et al.), WO 95/08629 (Mar. 30, 1995, by James E. Darnell, Jr. et al.) and United States application having a Ser. No. 08/212,184, filed on Mar. 11, 1994, entitled, "Interferon Associated Receptor Recognition Factors, Nucleic Acids Encoding the Same and Methods of Use Thereof" by James E. Darnell, Jr. et al., all of which are incorporated by reference in their entireties, herein. Currently, there are seven mammalian Stat family members which have been identified, numbered Stat 1, 2, 3, 4, 5A, 5B, and 6. Stat proteins include proteins derived from alternative splice sites such as Human Stat1α and Stat1β, i.e., Stat1β is a shorter protein than Stat1α and is translated from an alternatively spliced mRNA. Modified Stat proteins and functional fragments of Stat proteins are included in the present invention. One functional fragment is a truncated Stat protein defined below.

As used herein a the term "truncated Stat protein" denotes a Stat protein fragment having an N-terminal amino acid sequence that is substantially similar to the N-terminus of the corresponding full-length Stat protein following the cleavage of the proteolytic sensitive N-terminal domain from the corresponding full-length Stat protein. The carboxyl terminus of the truncated Stat protein extends at least to the phosphorylatable tyrosine required for homodimerization. Truncated Stat proteins are soluble proteins that can be phosphorylated, dimerize and bind to the DNA binding sites of the full-length Stat protein. An example of a truncated Stat protein is Stat1tc having the amino acid sequence of SEQ ID NO:3.

As used herein the terms "phosphorylated" and "nonphosphorylated" as used in conjunction with or in reference to a Stat protein denote the phosphorylation state of a particular tyrosine residue of the Stat proteins (e.g., Tyr 701 of Stat1). When Stat proteins are phosphorylated, they form homo- or heterodimeric structures in which the phosphotyrosine of one partner binds to the SRC homology domain (SH2) of the other. In their natural environment the newly formed dimer then translocates from the cytoplasm to the nucleus, binds to a palindromic GAS sequence, thereby activating transcription In a specific embodiment, two amino acid sequences of the truncated Stat protein are "substantially homologous" or "substantially similar" when at least about 75% (preferably at least about 90%, and most preferably at least about 95 or 98%) of the amino acids match over the defined length of the amino acid sequences; and the N-terminal domain of the corresponding full-length Stat protein is at least fifty percent deleted from both amino acid sequences. Analogously, two amino acid sequences of the Stat N-terminal peptide fragments are "substantially homologous" or "substantially similar" when at least about 75% (preferably at least about 90%, and most preferably at least about 95 or 98%) of the amino acids match over the defined length of the amino acid sequences; and the N-terminal peptide fragment can form homodimers. Sequences that are substantially homologous can be identified by comparing the sequences using standard software available in sequence data banks.

In a specific embodiment, two nucleotide sequences coding for the expression of the truncated Stat protein of the present invention are "substantially homologous" or "substantially similar" when at least about 50% (preferably at least about 75%, and most preferably at least about 90 or 95%) of the nucleotides match over the defined length of the nucleotide sequences; and the coding region for the N-terminal domain of the corresponding full-length Stat protein is at least fifty percent deleted (or frame-shifted from the coding region) from both nucleotide sequences. Sequences that are substantially homologous can be identified by comparing the sequences using standard software available in sequence data banks.

Purification and Characterization of the Stat Protein and the Truncated Stat Protein The Stat protein and truncated Stat protein of the present invention and homologues thereof can be purified as taught herein, using any number of alternative equivalent procedures that encompass a wide variety of known purification steps. Those with skill in the art would know to refer to references, such as the Methods of Enzymology series, for greater detail and breadth.

In a specific embodiment, exemplified below, a suitable procedure for purifying a Stat protein of the present invention is described as follows. One skilled in the art of protein purification would know that any such general procedure would probably need to be modified for any given Stat protein and as such, performing the requisite modifications would not be considered undue experimentation.

Expression and Purification of a Recombinant Stat Protein

Nucleic acids containing sequences coding for a Stat protein are amplified by PCR with primers containing restriction sites in addition to homologous sequence. The products are then cloned using the restriction sites into a baculovirus transfer vector, e.g. pAcSG2. Recombinant vectors are subsequently co-transfected with baculovirus DNA, such as Baculogold, into Sf9 insect cells. Recombinant viruses can be identified by immunoblot of extracts of the infected cells. For protein production Sf9 cells in a suspension culture (approximately $10^6$ cells/ml) are infected with recombinant viruses (multiplicity of infection: 1:5) and harvested by low speed centrifugation approximately two days following infection.

The resulting cells, generally in quantities of between $10^8$–$10^9$, are lysed in ice cold extraction buffer [approximately 80 mls of a low concentration Mes buffer (20–50 mM) containing, 100 mM KCl, 10 mM NaF, 0.02% $NaN_3$, 4 mM EDTA, 1 mM EGTA, 20 mM DTT, and Complete™ protease inhibitors (Boehringer Mannheim), pH adjusted with sodium hydroxide to pH 7.0] with a dounce homogenizer. All subsequent steps are performed at 4° C. unless noted otherwise. For optimal results all buffers used during protein purification are chilled, thoroughly degassed and flushed with $N_2$ before use.

The resulting lysates are cleared by low speed centrifugation. The supernatant is brought to about pH 6 after the addition of 0.5 vol of a buffer such as 20 mM Mes containing 0.02% $NaN_3$, 20 mM DTT, pH adjusted to about 6.0) and the supernatant is again centrifuged. The clarified supernatant is loaded onto a cation exchange resin, e.g., S-SEPHAROSE, in a short, fat column, e.g., 5×5.5 cm, and eluted with a linear salt gradient (50–300 mM monovalent salt) and pH gradient (pH 6–7). Fractions containing Stat protein are identified by, e.g., immunoblot, then pooled, and the pH of the pooled fractions are adjusted to 8.0 with 1M Tris. After the addition of 0.25 vol of a low concentration buffer such as 20 mM Tris-HCl containing 0.02% $NaN_3$, 10 mM DTT, at about pH 8, the solution is loaded onto an anionic exchange resin, such as Q-Sepharose, in a e.g., a 2×9 cm column. The Stat protein is eluted with a linear monovalent salt gradient from 100 mM to 300 mM. Eluted Stat protein is precipitated with solid ammonium sulfate to 60% saturation. The resulting concentrated Stat proteins are dissolved in about 10 ml of 50 mM phosphate buffer, pH 7.2, containing 2 mM DTT, 1 mM EDTA, and Complete™ protease inhibitors. The Stat protein is then alkylated. In one embodiment, alkylation is performed with N-ethyl-maleimide which is added to a final concentration of 20 mM. The alkylation reaction mixture is incubated at room temperature for 10 min and then placed on ice for another 30 min. The reaction is stopped by the addition of β-mercaptoethanol to 50 mM and ammonium sulfate to 0.5 M. The resulting reaction mixture is then loaded onto a low substituted Phenyl-Sepharose column (e.g., 2×15 cm) equilibrated in a low concentration buffer such as 20 mM Tris-HCl, about pH 7.4, containing 2 mM DTT plus 0.5 M ammonium sulfate. The Stat proteins are eluted with decreasing ammonium sulfate dissolved in the column equilibration buffer. Fractions containing Stat protein are pooled, and then concentrated to about 10 mg/ml using e.g., a centriprep 50. The concentrated sample is then applied to a gel filtration column, such as SUPERDEX 200 (XK 16, Pharmacia) equilibrated in low concentration buffer such as 20 mM Hepes-HCl, pH 7.2, containing 0.02% $NaN_3$, 2 mM DTT, and 0.3 M KCl. Fractions containing the Stat protein are pooled. The pooled fractions are then concentrated by ultrafiltration to approximately 20 mg/ml and quick frozen on dry ice. The purified proteins are stored at −70° C. When purifying substituted Stat protein containing converted cysteines, in which the cysteines that are involved in the inter-protein aggregation have been replaced, the alkylation step is left out. The procedure is otherwise analogous.

Expression and Purification of a Truncated Stat Protein

A portion of a Stat gene encoding a truncated Stat protein is amplified by PCR with primers containing restriction sites in addition to the desired sequence. The products are then cloned into a bacterial vector, e.g., the pET20b expression vector (Novagen) using these restriction sites. Growth and induction of transformed *E. coli* e.g., BL21DE3 (pLysS) is performed by standard procedures, such as described by Studier and Moffatt, 1986 (in this particular case the induction was carried out for 4 hours at 30° C. with 0.5 mM ITPG). Generally, about 50% of the induced protein remains soluble. This soluble truncated Stat protein is the isolatable form of the recombinant protein. Cells are collected by centrifugation and resuspended in ice cold extraction buffer at a concentration of about 30 g of cells to 100 mls of a low concentration buffer, e.g., 20 mM Hepes/HCl pH 7.6, containing 0.1 M KCl, 10% Glycerol, 1 mM EDTA, 10 mM $MnCl_2$, 20 mM DTT, 100 U/ml DNase I (Boehringer Mannheim), and Complete™ protease inhibitor. Cells are lysed by multiple cycles of freeze/thawing. Lysis is continued at 4° C. while stirring slowly for about an hour. The lysate is then centrifuged for about 20 min at about 20,000×g at 4° C. Polyethylenimine (0.1% final; Sigma) is added to the supernatant, the solution gently mixed and centrifuged for about 15 min at about 15,000×g. All subsequent steps are performed in the cold (4° C.) unless stated otherwise.

The supernatant containing the soluble truncated Stat protein is precipitated with saturated ammonium sulfate solution in two steps (0–35%; 35–55% saturation final). The 35–55% pellet is redissolved in about 20 ml of 50 mM phosphate buffer, pH 7.2, containing 2 mM DTT, 1 mM EDTA, and Complete™ protease inhibitors. The truncated Stat protein is then alkylated. In one embodiment, alkylation is performed with N-ethyl-maleimide which is added to a final concentration of 20 mM. The alkylation reaction mixture is incubated at room temperature for 10 min and then placed on ice for another 30 min. The reaction is stopped by the addition of β-mercaptoethanol to 50 mM and solid ammonium sulfate to 0.9 M. The mixture is then loaded onto a Fast Flow Phenyl-Sepharose column (low substituted, 2×15 cm) that had been equilibrated in buffer such as 50 mM Tris/HCl, pH 7.4 containing 1 mM EDTA, 0.02% $NaN_3$, 2 mM DTT, plus 0.9M ammonium sulfate. After washing the column, a linear decreasing salt gradient from 0.9 M to 0.05 M ammonium sulfate in the equilibration buffer, is applied. The truncated Stat protein elutes at about 0.5 M salt. The fractions containing truncated Stat protein are pooled and dialysed overnight against 2×4 liters of a buffer such as 40 mM Mes/NaOH pH 6.5, containing 10% Glycerol, 0.5 mM EDTA, 0.02% $NaN_3$, and 140 mM KCl. This material is loaded onto a cation exchange resin, e.g., S-Sepharose, in a short, fat column, e.g., 5×5.5 cm, and a linear 500 ml gradient of a buffer such as 40 MM Mes/NaOH pH 6.5, containing 10% Glycerol, 0.5 mM EDTA, 0.02% $NaN_3$ containing 140 mM to 300 mM KCl was applied. The protein generally elutes at approximately 220 mM KCl. Fractions containing the truncated Stat protein are collected and dialysed against 3 liters of a buffer such as 50 mM Tris/HCl, pH 8 containing 10% Glycerol, 2 mM DTT, and 50 mM KCl with one change of buffer. The protein solution is loaded onto an anionic exchange resin, such as Q-Sepharose, in a column e.g., a 2×9 cm and bound proteins are eluted with a linear gradient from 50 to 300 mM KCl in a buffer such as 50 mM Tris/HCl, pH 8 containing 10% Glycerol, 2 mM DTT. Fractions containing the truncated Stat protein are combined and precipitated with solid ammonium sulfate to 55% saturation. At this stage the 95% pure preparation can be stored at −20° C. until subjected to in vitro phosphorylation or is directly loaded onto a gel filtration column, such as Superdex 200 (XK 16; Pharmacia) equilibrated with 10 mM Hepes/HCl, 7.4 containing 100 mM KCl, 2 mM DTT, and 0.5 mM EDTA. In this case the precipitated protein is first dissolved in about 2 ml of 10 mM Hepes/HCl, 7.4 containing 100 mM KCl, 2 mM DTT, and 0.5 mM EDTA and then placed on the gel filtration column. The truncated Stat protein elutes in a symmetrical peak and is concentrated to a concentration of about 20 mg/ml using a Centriprep 50, for example, and quick frozen on dry ice. The pure alkylated truncated Stat protein is stored at −70° C. Typically yields of 40–50 mg (greater than 98% pure as judged by Coomassie blue stain and mass spectroscopy) of truncated Stat protein from 6 liters of starting culture can be obtained. Any person skilled in the art would know to scale-up this procedure when a greater quantity of Stat protein is needed, and to scale-down the procedure when less purified Stat protein is required.

When purifying substituted truncated Stat protein containing converted cysteines, in which the cysteines that are involved in the inter-protein aggregation have been replaced, the alkylation step is left out. The procedure is otherwise analogous.

One key aspect of the present invention need to be emphasized: the identification of a soluble truncated Stat protein that is crucial for preparing large amounts (30–50 mgs) of Stat protein in a single preparation. Heretofore, essentially all of the recombinant Stat protein expressed in a bacterial host, accumulated entirely in insoluble inclusion bodies. The present invention has overcome this problem by producing a truncated protein that is soluble in significant quantities.

Preparation of EGF-receptor Kinase and In vitro Phosphorylation of Stat Proteins Human carcinoma cells such as A431 cells, are grown to 90% confluency in 150 mm diameter plates in Dulbecco's modified Eagle's medium supplemented with 10% bovine calf serum. The cells are washed once with chilled phosphate buffered saline, PBS, and lysates are then conveniently prepared in about 1 ml of ice cold lysis buffer per plate, such as 10 mM Hepes/HCl, pH 7.5, containing 150 mM NaCl, 0.5% Triton X-100, 10% Glycerol, 1 mM $Na_3VO_4$, 10 mM EDTA and Complete™ protease inhibitors. After about 10 minutes on ice, the cells are scraped, vortexed and dounce homogenized. The lysates are cleared by centrifugation at 4° C., e.g., by centrifuging for 20 min at top speed in an Eppendorf microfuge. The resulting supernatant is stored at −70° C. until needed. Immediately before use, one volume of the lysates is mixed with four volumes of the lysis buffer forming diluted lysate.

EGF-receptor precipitates are obtained by incubating 5 ml of diluted lysate with about 50 $\mu$g of an anti-EGF-receptor monoclonal antibody directed against the extracellular domain. After two hours of rotating the sample at 4° C., 750 $\mu$l of Protein-A-agarose (50% slurry; Oncogene Science) is added, and the incubation proceeds while rotating, for about one more hour. Agarose beads containing the EGF-receptor immunoprecipitates are washed exhaustively (5–10 times) with lysis buffer and then at least twice more with a storage buffer such as 20 mM Hepes/HCl containing 20% Glycerol, 100 mM NaCl, and 0.1 mM $Na_3VO_4$. Precipitates from 5 ml diluted lysate are dissolved in 0.5 ml of the storage buffer, flash frozen on dry ice and stored at −70° C.

Immediately before the in vitro kinase reaction the Protein-A-agarose bound EGF-receptor from 5 ml dilute lysate is washed once with a 1× kinase buffer such as, 20 mM Tris/HCl, pH 8.0 containing 50 mM KCl, 0.3 mM $Na_3VO_4$, 2 mM DTT, pH 8.0 and then dissolved in 0.4 ml (total volume) of this buffer. Afterwards the washed EGF-receptor precipitate is incubated on ice for about 10 minutes in the presence of a final concentration of mouse EGF of 0.15 ng/$\mu$l. Phosphorylation reactions are conveniently carried out in Eppendorf tubes in a final volume of 1 ml. To the pre-incubated kinase preparation the following is added: 60 $\mu$l 10× kinase buffer, 20 $\mu$l 0.1 M DTT, 50 $\mu$l 0.1 M ATP, 4 mg purified Stat protein (e.g., the Superdex 200 eluate for Stat proteins; and ammonium sulfate pellets dissolved in 20 mM Tris/HCl, pH 8.0 for the truncated Stat protein of the preparations described above), 10 $\mu$l 1M $MnCl_2$ and distilled water is added to 1 ml. The reaction is allowed to proceed for about 15 hours at 4° C. After 3 hours an additional 15 $\mu$l of 0.1 M ATP is added.

Separation of Phosphorylated from Unphosphorylated Stat Proteins

The in vitro kinase reaction mixture (above) is freed from the EGF-receptor bound to agarose beads by washing the beads and physically separating the eluate from the beads. This may be conveniently performed by spinning the mixture through a plug of siliconized glass wool at the bottom of a pierced Eppendorf tube. The glass wool is washed with 0.5 ml of a buffer, such as 20 mM Tris/HCl, pH 8.0, containing 1 mM EDTA, and 2 mM DTT. This buffer is also used to equilibrate a heparin agarose column, (HA-buffer). The pooled volumes from the glass wool eluate are loaded onto the equilibrated heparin agarose column (1.5×7 cm) and the column is washed with about 50 ml HA-buffer plus 50 mM KCl. The bound Stat proteins or truncated Stat proteins are eluted with two consecutive 50 ml volumes of HA-buffer plus a moderate salt concentration such as 150 mM KCl and then HA-buffer plus a higher salt concentration such as 400 mM KCl. Unphosphorylated proteins generally elute at the moderate salt concentration and are then concentrated e.g., by ultrafiltration to about 10 mg/ml, flash frozen on dry ice and stored at −70° C. Phosphorylated Stat proteins generally elute at the higher salt concentration and are concentrated to about 1 mg/ml. Glycerol is added to about 50% (vol/vol) and the material is stored at −20° C.

Phosphorylated truncated Stat protein is brought to a concentration of about 15 mg/ml. The concentrated sample is then applied to a gel filtration column, such as Superdex 200 (XK 16, Pharmacia) equilibrated in low concentration buffer such as 20 mM Hepes-HCl, pH 7.2, containing 0.02% $NaN_3$, 2 mM DTT, and 0.3 M KCl. Fractions containing the gel filtered phosphorylated truncated Stat protein are pooled, concentrated to approximately 20 mg/ml, flash frozen on dry ice and stored at −70° C.

General Techniques for Constructing Nucleic Acids That Express Recombinant Stat Proteins In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences and synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease SI), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "homologous" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins have sequence homology as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding Stat protein, whether genomic DNA or cDNA, can be isolated from any animal source, particularly from a mammal. Methods for obtaining the Stat protein gene are well known in the art, as described above (see, e.g., Sambrook et al., 1989, supra).

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

The present invention also relates to cloning vectors containing genes encoding analogs and derivatives of the Stat protein, including the truncated Stat protein, of the invention, that have the same or homologous functional activity as Stat protein, and homologs thereof. The production and use of derivatives and analogs related to the Stat protein are within the scope of the present invention.

Stat protein derivatives and analogs as described above can be made by altering encoding nucleic acid sequences by substitutions, e.g. replacing a cysteine with a threonine, additions or deletions that provide for functionally equivalent molecules. Preferably, derivatives are made that have enhanced or increased functional activity relative to native Stat protein. Alternatively, such derivatives may encode soluble recombinant fragments of Stat protein such as Stat1tc having an amino acid sequence of SEQ ID NO:3.

Due to the degeneracy of nucleotide coding sequences, other DNA sequences which encode substantially the same amino acid sequence as a truncated Stat protein gene may be used in the practice of the present invention. These include but are not limited to allelic genes, homologous genes from other species, which are altered by the substitution of different codons that encode the same amino acid residue within the sequence, thus producing a silent change. Likewise, the truncated Stat protein derivatives of the invention include, but are not limited to, those containing, as a primary amino acid sequence, all or part of the amino acid sequence of a truncated Stat protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding Stat proteins, truncated Stat protein and derivatives and analogs thereof can be produced by various methods known in the art. The manipulations which result in their production can occur at the gene or protein level. For example, the cloned truncated Stat protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a Stat protein or a truncated Stat protein, care should be taken to ensure that the modified gene remains within the same translational reading frame as the Stat protein gene, uninterrupted by translational stop signals, in the gene region where the desired activity is encoded.

Additionally, the Stat or truncated Stat protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity or isolatability of the mutated truncated or native Stat protein gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Stat Proteins

The nucleotide sequence coding for a Stat protein, or functional fragment, including the truncated Stat protein and the N-terminal peptide fragment of a Stat protein, derivatives or analogs thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding a Stat protein of the invention or functional fragment, including the truncated Stat protein and the N-terminal peptide fragment of a Stat protein, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector. As detailed below, all genetic manipulations described for the Stat gene in this section, may also be employed for genes encoding a functional fragment, including the truncated Stat protein and the N-terminal peptide fragment of a Stat protein, derivatives or analogs thereof, including a chimeric protein, thereof.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant Stat protein of the invention, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding Stat protein is cultured in an appropriate cell culture medium under conditions that provide for expression of Stat protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of Stat protein may be controlled by any promoter/enhancer element known in the art, but these regulatory elements must be functional in the host selected for expression. Promoters which may be used to control Stat protein gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Expression vectors containing a nucleic acid encoding a Stat protein of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding Stat protein is inserted within the "selection marker" gene sequence of the vector, recombinants containing the Stat protein insert can be identified by the absence of the Stat protein gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *E. coli* plasmids col E1, pCR1, pBR322, pMa1-C2, pET, pGEX (Smith et al., 1988, Gene 67:31–40), pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology*, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express OB polypeptide. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

General Protein Purification Procedures

Initial steps for purifying the proteins of the present invention include salting in or salting out, such as in ammonium sulfate fractionations; solvent exclusion fractionations, e.g., an ethanol precipitation; detergent extractions to free membrane bound proteins using such detergents as Triton X-100, Tween-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSEPHAROSE and a high salt buffer; affinity-binding, using, e.g., placing a specific DNA binding site of a Stat protein to an activated support; immuno-binding, using e.g., an antibody to the Stat protein bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations are used. Low concentration buffers generally infer 5–25 mM concentrations. High concentration buffers generally infer concentrations of the buffering agent of between 0.1–2M concentrations. Typical buffers can be purchased from most biochemical catalogues and include the classical buffers such as Tris, pyrophosphate, monophosphate and diphosphate. The Good buffers [Good, N. E., et al.,(1966) Biochemistry, 5, 467; Good, N. E. and Izawa, S., (1972) Meth. Enzymol., 24, Part B, 53; and Fergunson, W. J. and Good, N. E., (1980) Anal. Biochem. 104, 300.] such as Mes, Hepes, Mops, tricine and Ches.

Materials to perform all of these techniques are available from a variety of sources such as Sigma Chemical Company in St. Louis, Mo.

Synthetic Polypeptides and Fragments Thereof

The term "polypeptide" is used in its broadest sense to refer to a compound of two or more subunit amino acids, amino acid analogs, or peptidomimetics. The subunits may be linked by peptide bonds. In another embodiment, the subunit may be linked by other the bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The Stat proteins and active fragments thereof, including the truncated Stat protein of the present invention may be chemically synthesized. In addition, potential drugs that may be tested in the drug screening assays of the present invention may also be chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^\alpha$-amino protected $N^\alpha$-t-butyloxycarbonyl) amino acid resin with the standard deprotecting, neutralization, coupling and wash protocols of the original solid phase procedure of Merrifield (1963, J. Am. Chem. Soc. 85:2149–2154), or the base-labile $N^\alpha$-amino protected 9-fluorenylmethoxycarbonyl (Fmoc) amino acids first described by Carpino and Han (1972, J. Org. Chem. 37:3403–3409). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics, and peptidomimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189–199; Hruby et al., 1990, Biochem J. 268:249–262); the present invention provides a method to produce a constrained peptide that incorporates random sequences at all other positions.

Constrained and Cyclic Peptides

A constrained, cyclic or rigidized peptide may be prepared synthetically, provided that in at least two positions in the sequence of the peptide an amino acid or amino acid analog is inserted that provides a chemical functional group capable of crosslinking to constrain, cyclise or rigidize the peptide after treatment to form the crosslink. Cyclization will be favored when a turn-inducing amino acid is incorporated. Examples of amino acids capable of crosslinking a peptide are cysteine to form disulfides, aspartic acid to form a lactone or a lactam, and a chelator such as γ-carboxyl-glutamic acid (Gla) (Bachem) to chelate a transition metal and form a cross-link. Protected γ-carboxyl glutamic acid may be prepared by modifying the synthesis described by Zee-Cheng and Olson (1980, Biophys. Biochem. Res. Commun. 94:1128–1132). A peptide in which the peptide sequence comprises at least two amino acids capable of crosslinking may be treated, e.g., by oxidation of cysteine residues to form a disulfide or addition of a metal ion to form a chelate, so as to crosslink the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137–167; Ponsanti et al., 1990, Tetrahedron 46:8255–8266). The first pair of cysteines may be deprotected and oxidized, then the second set may be deprotected and oxidized. In this way a defined set of disulfide cross-links may be formed. Alternatively, a pair of cysteines and a pair of chelating amino acid analogs may be incorporated so that the cross-links are of a different chemical nature.

Non-classical Amino Acids that Induce Conformational Constraints

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275–2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53–76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834–5838); β-sheet inducing analogs (Kemp et al., 1988, Tetrahedron Lett. 29:5081–5082); β-turn inducing analogs (Kemp et al., 1988, Tetrahedron Lett. 29:5057–5060); α-helix inducing analogs (Kemp et al., 1988, Tetrahedron Lett. 29:4935–4938); γ-turn inducing analogs (Kemp et al., 1989, J. Org. Chem. 54:109:115); and analogs provided by the following references: Nagai and Sato, 1985, Tetrahedron Lett. 26:647–650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853–3856); tretrazol (Zabrocki et al., 1988, J. Am. Chem. Soc. 110:5875–5880); DTC (Samanen et al., 1990, Int. J. Protein Pep. Res. 35:501:509); and analogs taught in Olson et al., 1990, J. Am. Chem. Sci. 112:323–333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

Derivatized and Modified Peptides

The present invention further provides for modification or derivatization of a peptide of the invention. Modifications of peptides are well known to one of ordinary skill, and include phosphorylation, carboxymethylation, and acylation. Modifications may be effected by chemical or enzymatic means.

In another aspect, glycosylated or fatty acylated peptide derivatives may be prepared. Preparation of glycosylated or fatty acylated peptides is well known in the art as exemplified by the following references:

1. Garg and Jeanloz, 1985, in Advances in Carbohydrate Chemistry and Biochemistry, Vol. 43, Academic Press.
2. Kunz, 1987, in Ang. Chem. Int. Ed. English 26:294–308.
3. Horvat et al., 1988, Int. J. Pept. Protein Res. 31:499–507.
4. Bardaji et al., 1990, Ang. Chem. Int. Ed. English, 23:231.
5. Toth et al., 1990, in Peptides: Chemistry, Structure and Biology, Rivier and Marshal, eds., ESCOM Publ., Leiden, pp. 1078–1079.
6. Torres et al., 1989, Experientia 45:574–576.
7. Torres et al., 1989, EMBO J. 8:2925–2932.
8. Hordever and Musiol, 1990, in Peptides: Chemistry, Structure and Biology, loc. cit., pp. 811–812.
9. Zee-Cheng and Olson, 1989, Biochem. Biophys. Res. Commun. 94:1128–1132.
10. Marki et al., 1977, Helv. Chem. Acta., 60:807.
11. Fuju et al. 1987, J. Chem. Soc. Chem. Commun., pp. 163–164.
12. Ponsati et al., 1990, Peptides 1990, Giralt and Andreu, eds., ESCOM Publ., pp. 238–240.
13. Fuji et al., 1987, 1988, Peptides: Chemistry and Biology, Marshall, ed., ESCOM Publ., Leiden, pp. 217–219.

There are two major classes of peptide-carbohydrate linkages. First, ether bonds join the serine or threonine hydroxyl to a hydroxyl of the sugar. Second, amide bonds join glutamate or aspartate carboxyl groups to an amino group on the sugar. In particular, references 1 and 2, supra, teach methods of preparing peptide-carbohydrate ethers and amides. Acetal and ketal bonds may also bind carbohydrate to peptide.

Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure—$(CH_2)_n CH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Phage Libraries for Drug Screening

Phage libraries have been constructed which when infected into host *E. coli* produce random peptide sequences of approximately 10 to 15 amino acids [Parmley and Smith, Gene 73:305–318 (1988), Scott and Smith, Science 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive N-terminal peptide fragment of a Stat protein (e.g., the fragment having the amino acid sequence of SEQ ID NO:4). After a specified incubation period, the filters can be thoroughly washed and developed for autoradiography. Plaques containing the phage that bind to the radioactive N-terminal peptide fragment of a Stat protein can then be identified. These phages can be further cloned and then retested for their ability to bind to the N-terminal peptide fragment of a Stat protein as before. Once the phages have been purified, the binding sequence contained within the phage can be determined by standard DNA sequencing techniques. Once the DNA sequence is known, synthetic peptides can be generated which represents these sequences.

These peptides can be tested, for example, for their ability to: (1) interfere with a Stat protein binding to its DNA binding site; and (2) interfere with a truncated Stat protein binding to the DNA binding site. If the peptide interferes in the first case but does not interfere in the latter case, it may be concluded that the peptide interferes with N-terminal inter-protein interaction of Stat proteins.

The effective peptide(s) can be synthesized in large quantities for use in in vivo models and eventually in humans to prevent modulate signal transduction. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, Vaccine 10:175–178 (1990)].

Antibodies to the Truncated Stat Protein

According to the present invention, the truncated Stat protein as purified from recombinant sources or produced by chemical synthesis, and derivatives or analogs thereof, including fusion proteins, may be used as an immunogen to generate antibodies that recognize the truncated Stat protein. Such antibodies include but are not limited to polyclonal, monoclonal, chimeric, single chain, Fab fragments, and a Fab expression library. The anti-truncated Stat protein antibodies of the invention may be cross reactive, that is, they may recognize the truncated Stat protein derived from different natural Stat proteins such as Human Stat1α, Human Stat 6 or a Drosophila Stat protein. Polyclonal antibodies have greater likelihood of cross reactivity. Alternatively, an antibody of the invention may be specific for a single form of the truncated Stat, such as the Human Stat1tc having an amino acid sequence of SEQ ID NO:3.

Various procedures known in the art may be used for the production of polyclonal antibodies to the truncated Stat protein or derivative or analog thereof. For the production of antibody, various host animals can be immunized by injection with the truncated Stat protein, or a derivative (e.g., or fusion protein) thereof, including but not limited to rabbits, mice, rats, sheep, goats, etc. In one embodiment, the truncated Stat protein can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the truncated Stat protein, or analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an truncated Stat protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce truncated Stat protein-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for a truncated Stat protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of the truncated Stat protein, one may assay generated hybridomas for a product which binds to the truncated Stat protein fragment containing such epitope. For selection of an antibody specific to the truncated Stat protein from a particular source, one can select on the basis of positive binding with truncated Stat protein expressed by or isolated from that specific source.

The foregoing antibodies can be used in methods known in the art relating to the localization and activity of the truncated Stat protein, e.g., for Western blotting, imaging truncated Stat protein in situ, measuring levels thereof in appropriate physiological samples, etc. using any of the detection techniques mentioned above or known in the art.

In a specific embodiment, antibodies that agonize or antagonize the activity of truncated Stat protein can be generated. Such antibodies can be tested using the assays described infra for identifying ligands.

Labels

Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70. 419–439, 1980 and in U.S. Pat. No. 4,857,453.

Suitable enzymes include, but are not limited to, alkaline phosphatase and horseradish peroxidase.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^3H]$-amino acids (with the tritium substituted at non-labile positions).

Binding Assays for Drug Screening Assays

The drug screening assays of the present invention may use any of a number of assays for measuring the stability of a protein-protein interaction, including fragments thereof, or a protein-DNA binding interaction. In one embodiment the stability of preformed DNA protein complex between a Stat protein and its corresponding DNA binding site is examined as follows: the formation of a complex between the Stat protein and a labelled oligonucleotides is allowed to occur and unlabelled oligonucleotides are added in vast molar excess after the reaction reaches equilibrium. At various times after the addition of unlabelled competitor DNA, aliquots are layered on a running native polyacrylamide gel to determine free and bound oligonucleotides. In one preferred embodiment the protein is Stat1α, and two different labelled DNAs are used, the natural cfos site, an example of a "weak" site, and the mutated cfos-promotor element (M67) an example of a "strong" site as described below. Other examples of weak sites include those in the promoter of the MIG gene, and those in the regulatory region of the interferon-γ gene. Other examples of strong sites include those from the promoter of the Ly6E gene or the promoter of the IRF-1 gene.

In other binding assays, an N-terminal fragment of the Stat protein is placed or coated onto a solid support. Methods for placing the N-terminal fragment on the solid support are well known in the art and include such things as linking biotin to the fragment and linking avidin to the solid support. The corresponding free N-terminal fragment is allowed to equilibrate with the bound fragments and drugs are tested to see if they disrupt or enhance the dimer binding. Disruption leads to either a faster release of the free N-terminal fragment which may be expressed as a faster off time, and or a greater concentration of released fragment. Enhancement leads to either a slower release of the free N-terminal fragment which may be expressed as a slower off time, and or a lower concentration of released fragment.

The N-terminal fragment may be labeled as described above. For example, in one embodiment radiolabled N-terminal fragments are used to measure the effect of a drug on binding. In another embodiment the natural ultraviolet absorbance of the free N-terminal fragments is used. In yet another embodiment, a Biocore chip (Pharmacia) coated with the N-terminal fragment of a Stat protein is used and the change in surface conductivity can be measured.

Drug screening assays may also be performed in cells which are induced to contain activated STAT proteins, which are dimeric STAT proteins. Although cells that naturally encode the STAT proteins may be used, preferably a cell is used that is transfected with a plasmid encoding the STAT protein. For example transient transfections can be performed with 50% confluent U3A cells using the calcium phosphate method as instructed by the manufacturer (Stratagene). In addition the cells can also be modified to contain one or more reporter genes, a heterologous gene encoding a reporter such as luciferase, green fluorescent protein or derivative thereof, chloramphenicol acetyl transferase, β-galactosidase, etc. Such reporter genes can individually be operably linked to promoters comprising two weak STAT binding sites and/or a promoter comprising a strong STAT binding site. Assays for detecting the reporter gene products are readily available in the literature for example, luciferase assays can be performed according to the manufacturer's protocol (Promega), and β-galactosidase assays can be performed as described by Ausubel et al., [in *Current Protocols in Molecular Biology*, J. Wiley & Sons, Inc. (1994)].

In one example, the transfection reaction can comprise the transfection of a cell with a plasmid modified to contain a STAT protein, such as a pcDNA3 plasmid (Invitrogen), a reporter plasmid that contains a first reporter gene, and a reporter plasmid that contains a second reporter gene. Although the preparation of such plasmids is now routine in the art, many appropriate plasmids are commercially available e.g., a plasmid with β-galactosidase is available from Stratagene.

The reporter plasmids can contain specific restriction sites in which an enhancer element having a strong STAT binding site or alternatively two tandemly arranged "weak" STAT binding sites are inserted. In one particular embodiment, thirty-six hours after transfection of the cells with a plasmid encoding STAT-1, the cells are treated with 5 ng/ml interferon-γ Amgen for ten hours. Protein expression and tyrosine phosphorylation (to monitor STAT activation) can be determined by e.g., gel shift experiments with whole cell extracts.

Cells containing a STAT protein and a reporter gene that is operably linked to a promoter comprising two weak STAT binding sites can be contacted with a prospective drug in the presence of a cytokine which activates the STAT(s) of interest. The amount of reporter produced in the absence and presence of prospective drug is determined and compared. Prospective drugs which reduce the amount of reporter produced are candidate antagonists of the N-terminal interaction, whereas prospective drugs which increase the amount of reporter produced are candidate agonists. Cells containing a reporter gene operably linked to a promoter comprising a strong STAT binding site are then contacted with these candidate drugs, in the presence of a cytokine which activates the STAT(s) of interest. The amount (and/or activity) of reporter produced in the presence and absence of candidate drugs is determined and compared. Drugs which disrupt interactions between the N-terminal domains of the STATs will not reduce reporter activity in this second step. Similarly, candidate drugs which enhance interactions between N-terminal domains of STATs will not increase reporter activity in this second step.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

DNA Binding of In vitro Activated Purified Stat1α, Stat1β and truncated Stat1: Interaction between $NH_2$, Terminal Domains Stabilizes Binding of Two Dimers to Tandem DNA Sites Introduction To conveniently study the biochemistry of activated Stat molecules, it is necessary not only to use recombinant DNA techniques to produce large amounts of protein, but it is also necessary to phosphorylate the correct tyrosine residue and to separate the phosphorylated and nonphosphorylated proteins. The present invention teaches proteins, nucleic acids, and methods that satisfy these heretofore, unattained criteria.

Human Stat1α and Stat1β, a shorter protein translated from an alternatively spliced mRNA, were produced in insect cells infected with recombinant baculovirus, thereby allowing milligram amounts of these proteins to be isolated at a time. The protease sensitivity of purified Stat1α was subsequently studied. A stable truncated form of Stat1 (Stat1tc) was then characterized and produced in bacteria. Stat1α, Stat1β and Stat1tc were quantitatively phosphorylated in vitro with immunoprecipitated, activated EGF-receptor kinase. The phosphoproteins were isolated in milligram quantities by a new chromatographic protocol, and the phosphorylation was shown to be on the correct tyrosine residue by mass spectroscopy of Stat1 fragments. Both the full length and the truncated phosphorylated protein dimerize and bind to DNA.

With the purified activated DNA binding form of Stat1 available, its DNA binding characteristics were studied. A KD of about $1 \times 10^{-9}$ M for a variety of recognition sequences was determined. By examining the stability of labelled preformed protein/DNA complexes when challenged with unlabelled DNA, we found a very short half-life of the protein/DNA complexes. For sites that showed the maximum binding stability, we determined a half-life, $t_{1/2}$, of about 3 min. A more rapid exchange (half-life of <30 sec) was observed for both Stat1α or Stat1tc bound to the sites that are natural "weak" binding sites in genomic DNA. Stat1 dimers (Guyer et al., 1995) or dimers of Drosophila Stat protein (D-Stat) (Yan et al., 1996) may interact when two nearby Stat binding sites are both occupied. The purified activated human protein behaves in a similar manner based on evidence of interaction between bound dimeric molecules in which the binding of Stat dimers to adjacent DNA binding sites was stabilized when both sites were occupied. Furthermore this proposed Stat dimer interaction is dependent on the presence of the amino terminal 131 amino acids of Stat1.

Materials and Methods

Expression and Purification of Stat1α and Stat1β

Nucleic acids containing sequences coding for human Stat1α and Stat1β were amplified by PCR (primers containing respective restriction sites in addition to homologous sequence; Vent-polymerase; New England Biolabs) and the products cloned into the StuI/BglII (Stat1α) or EcoRI/KpnI (Stat1β)—sites of the baculovirus transfer vector pAcSG2 (Pharmingen). Recombinant vectors were subsequently co-transfected with Baculogold baculovirus DNA (Pharmingen) into Sf9 insect cells as described (Gruenwald and Heitz, 1993). Recombinant viruses were identified by immunoblot of extracts of infected cells. For protein production Sf9 cells in suspension culture ($0.8 \times 10^6$ cells/ml) were infected with recombinant viruses (mean of infection: 1.5) and harvested by centrifugation (1500×g, 15 min) 50 h post infection.

The cells ($5–8 \times 10^8$) were lysed in 80 ml ice cold extraction buffer [20 mM Mes, 100 mM KCl, 10 mM NaF, 10 mM $Na_2HPO_4/NaH_2PO_4$ pH 7.0, 10 mM NaPPi, 0.02% $NaN_3$, 4 mM EDTA, 1 mM EGTA, 20 mM DTT, Complete™ protease inhibitors (Boehringer Mannheim), pH adjusted to 7.0 with 1 M Tris] with a dounce homogenizer (2×10 strokes). All subsequent steps were performed at 4° C. unless noted otherwise. Lysates were cleared by centrifugation at 20,000×g for 30 min. The supernatant was brought to pH 6.2 with 1 M Mes and after the addition of 0.5 vol buffer 1 (20 mM Mes, 0.02% $NaN_3$, 20 mM DTT, pH adjusted to 6.0 with 1 M Tris) it was again centrifuged for 20 min at 25,000×g. The resulting supernatant was loaded onto a S-Sepharose (Pharmacia) column (5×5.5 cm) and eluted with a linear salt gradient (50–300 mM KCl) and pH gradient (pH 6–7). Stat protein containing fractions, identified by immunoblot, were pooled, the pH adjusted to 8.0 with 1 M Tris and after the addition of 0.25 vol buffer 2 (20 mM Tris/HCl, 0.02% $NaN_3$, 10 mM DTT, pH 8.0) loaded onto a Q-Sepharose (Pharmacia) column (2×9 cm). This column was developed with a linear KCl gradient from 100 mM to 300 mM KCl. Eluted Stat1 proteins were precipitated with solid $(NH_4)_2SO_4$ to 60% saturation. The concentrated Stat proteins were dissolved in ~10 ml of buffer 3 [50 mM $Na_2HPO_4/NaH_2PO_4$ pH 7.2, 2 mM DTT, 1 mM EDTA, Complete™ protease inhibitors]. N-ethyl-maleimide (Sigma) was added to a final concentration of 20 mM. The alkylation reaction mixture was incubated at room temperature for 10 min and then placed on ice for another 30 min. The reaction was stopped by the addition of β-mercaptoethanol to 50 mM and $(NH_4)_2SO_4$ to 0.5 M. The reaction mixture was then loaded onto a low substituted Phenyl-Sepharose (Pharmacia) column (2×15 cm) equilibrated in buffer 4 (20 mM Tris/HCl, 2 mM DTT, pH 7.4)+0.5 M ammonium sulfate and the Stat proteins were eluted with decreasing $(NH_4)_2SO_4$ in buffer 4. (The Stat proteins eluted at about 300 mM salt). Fractions of interest were pooled, concentrated by centriprep 50 (Amicon) to about 10 mg/ml and applied to a SUPERDEX 200 column (XK 16, Pharmacia) equilibrated in buffer 5 (20 mM Hepes/HCl, 0.02% $NaN_3$, 2 mM DTT, 0.3 M KCl, pH 7.2). Fractions containing Stat1α or Stat1β were pooled. Both Stat1α and Stat1β eluted very early, e.g. with a volume typical for globular proteins of $M_r$ 350 kD. The pooled fractions were then concentrated by ultrafiltration to approximately 20 mg/ml and quick frozen on dry ice. The purified proteins were stored at −70° C. All buffers used during protein purification were chilled, thoroughly degassed and flushed with $N_2$ before use.

Expression and Purification of Stat1tc

The portion of the human Stat1 gene encoding residues 132–713 was amplified by PCR (Vent-Polymerase). The following primers were used: 5'-dGGGAATTC<u>CATATG</u>AGCACAGTGATG-TTAGACAAAC (SEQ ID NO:7) and 5'-dCGGATCCTATTAGTGAACTTCAGACACAGAAATC (SEQ ID NO:8) (restriction sites underlined). The product was cloned into the NdeI/BamHI sites of the pET20b expression vector (Novagen). N-terminal sequencing revealed the absence of the methionine residue introduced with the NdeI restriction site. Growth and induction of transformed E. coli [BL21DE3 (pLysS)] was as described (Studier and Moffatt, 1986). About 50% of the induced protein remained soluble and was subsequently isolated. Cells were collected by centrifugation (20 min; 4° C.; 20,000 g) and resuspended in ice cold extraction buffer (100 ml/30 g cells; 20 mM Hepes/HCl, 0.1 M KCl, 10% Glycerol, 1 mM EDTA, 10 mM $MnCl_2$, 20 mM DTT, 100 U/ml DNase I (Boehringer Mannheim), Complete™ protease inhibitor, pH 7.6). Cells were lysed by three cycles of freeze/thawing. Lysis was continued at 4° C. while stirring slowly for 1 h. The lysate was centrifuged for 20 min at 22,000×g at 4° C. Polyethylenimine (0.1% final; Sigma) was added to the supernatant, the solution gently mixed and centrifuged for 15 min at 15,000×g. All subsequent steps were performed in the cold (4° C.) unless stated otherwise. The supernatant containing soluble Stat1tc was precipitated with saturated ammonium sulfate solution (ultrapure; Gibco) in two steps (0–35%; 35–55% saturation final). The 35–55% pellet was redissolved in 20 ml of buffer 3 (see above) and alkylated as described above. The reaction was stopped by the addition of β-mercaptoethanol to 50 mM and solid ammonium sulfate to 0.9 M. The mixture was loaded onto a Fast Flow Phenyl-SEPHAROSE column (low substituted, 2×15 cm) that had been equilibrated in buffer A (50 mM Tris/HCl, 1 mM EDTA, 0.02% $NaN_3$, 2 mM DTT, pH 7.4)+0.9 M ammonium sulfate. After washing the column a linear gradient from 0.9 M to 0.05 M ammonium sulfate in buffer A was applied. Stat1tc eluted at about 0.5 M salt and the Stat1tc containing fractions were pooled and dialysed overnight against 2×4 liters of buffer B (40 mM Mes/NaOH, 10% Glycerol, 0.5 mM EDTA, 0.02% $NaN_3$, pH 6.5)+140 mM KCl. This material was loaded onto a S-Sepharose column (5×5.5 cm) and a linear 500 ml gradient of buffer B containing 140 mM to 300 mM KCl was applied. The protein eluted in at approximately 220 mM KCL. Fractions of interest were collected and dialysed against 3 liters of buffer C (50 mM Tris/HCl, 10% Glycerol, 2 mM DTT, pH 8)+50 mM KCl with one change of buffer. The protein solution (in buffer C+50 mM KCl) was then applied to a Q-Sepharose column (2×9 cm) and bound proteins were eluted with a linear gradient from 50 to 300 mM KCl in buffer C. Fractions with Stat1tc were combined and precipitated with solid ammonium sulfate to 55% saturation. At this stage the 95% pure preparation could be stored at −20° C. until subjected to in vitro phosphorylation (see below) or was directly loaded onto a SUPERDEX 200 gel filtration column (XK 16; Pharmacia). In this case the precipitated protein was dissolved in about 2 ml of 10 mM Hepes/HCl, 100 mM KCl, 2 mM DTT, 0.5 mM EDTA, pH 7.4 and gel filtrated in this buffer. Stat1tc eluted in a symmetrical peak and was concentrated to about 20 mg/ml (Centriprep 50), quick frozen on dry ice and stored at −70° C. Typically yields of 40–50 mg (greater than 98% pure as judged by Coomassie stain and mass spectroscopy) Stat1tc from 6 liters of starting culture could be obtained.

Determination of Protein Concentrations

Purified proteins were quantitated by UV spectroscopy. The extinction coefficient ε in a 1 cm path length for a 1 mg/ml solution of protein can be estimated by the formula $[(5700 \times W + 1300 \times Y)/M_r]$ with W=number of tryptophans;

Y=number of tyrosines and $M_r$=molecular weight (Cantor and Schimmel, 1980). The following extinction values ($mM^{-1}cm^{-1}$) were used: Stat1α: ε=1.25; Stat1β: ε=1.31; Stat1tc: ε=1.27.

Proteolytic Digestion of Stat1α and Amino-terminal Sequencing of Fragments

Proteinase K and subtilisin (Sigma) digests of purified Stat1α were carried out for 30 minutes on ice. The protein was digested at the concentration of 4.5 μM in 50 μl of cleavage buffer which contained 20 mM Hepes/HCl, 50 mM ammonium sulfate, and 10 mM $MgCl_2$, pH 7.4.

Reactions were stopped by the addition of PMSF (2 mM final) and SDS-sample buffer. The proteolysis was resolved on a 10% or 16.5% SDS PAGE gel, which was either stained with Coomassie blue or electro-transferred onto a PVDF membrane(Immobilon $P^{SQ}$; Millipore). Sequencing of the amino terminus of the 65 kDa protease resistent Stat1α fragment was performed as described by LeGendre and Matsudaira, (1988). Amino terminal sequence analysis was performed by the Protein/DNA facilities at The Rockefeller University.

Cyanogen Bromide and Endoproteinase AspN Digests with Mass Spectrometric Peptide Analysis Cyanogen bromide (Sigma) digests were performed on 90 pmol of recombinant protein in 50% formic acid at 25° C. in the dark. Endoproteinase AspN (sequencing grade; Boehringer Mannheim) digests were carried out on 100–150 pmol of protein in either 25 mM Tris/HCl (pH 7.5) or 10 mM ammonium phosphate buffer (pH 8) with 150 mM KCl at 25° C. The protease:protein ratio was 1:50 by weight, e.g., 0.2 μg: 10 μg. Matrix-assisted laser desorption/ionization mass spectrometry (MALDI-MS) was used to evaluate the peptide fragments. Aliquots (0.5 μl) of the digest were taken at various intervals (1 min to 7 hours), directly mixed into the MALDI-MS matrix solution (Cohen and Chait, 1996), and subject to MALDI-MS analysis in a procedure reported earlier (Cohen et al., 1995).

Preparation of EGF-receptor Kinase and In vitro Phosphorylation of Stat Proteins Human carcinoma A431 cells were grown to 90% confluency in 150 mm diameter plates in Dulbecco's modified Eagle's medium supplemented with 10% bovine calf serum (Hyclone). Cells were washed once with chilled PBS and lysates were prepared in 1 ml ice cold lysis buffer (10 mM Hepes/HCl, 150 mM NaCl, 0.5% Triton X-100, 10% Glycerol, 1 mM $Na_3VO_4$, 10 mM EDTA, Complete™ protease inhibitors, pH 7.5). After 10 min on ice, the cells were scraped, vortexed and dounce homogenized (5 strokes). The lysates were cleared by centrifugation at 4° C. for 20 min at top speed in an Eppendorf microfuge and stored at −70° C. until needed. Immediately before use 1 volume of the lysate was diluted with 4 volumes of the lysis buffer ("diluted lysate").

EGF-receptor precipitates were obtained by incubating 5 ml of diluted lysate with 50 μg of an anti-EGF-receptor monoclonal antibody directed against the extracellular domain. After 2 hours of rotating the sample at 4° C., 750 μl of Protein-A-agarose (50% slurry; Oncogene Science) was added, and the incubation was allowed to proceed, while rotating, for another 1 hour. Agarose beads containing the EGF-receptor immunoprecipitates were then washed 5 times with lysis buffer and finally twice with storage buffer (20% Glycerol, 20 mM Hepes/HCl, 100 mM NaCl, 0.1 mM $Na_3VO_4$). Precipitates from 5 ml diluted lysate were dissolved in 0.5 ml storage buffer, flash frozen on dry ice and stored at −70° C. Immediately before an in vitro kinase reaction the Protein-A-agarose bound EGF-receptor from 5 ml dilute lysate was washed once with 1× kinase buffer (20 mM Tris/HCl, 50 mM KCl, 0.3 mM $Na_3VO_4$, 2 mM DTT, pH 8.0) plus 50 mM KCL and then dissolved in 0.4 ml (total volume) of this buffer. Afterwards the washed EGF-receptor precipitate was incubated on ice for 10 min in the presence of a final concentration of mouse EGF of 0.15 ng/μl. Phosphorylation reactions were carried out in Eppendorf tubes in a final volume of 1 ml. To the pre-incubated kinase preparation the following was added: 60 μl 10× kinase buffer, 20 μl 0.1 M DTT, 50 μl 0.1 M ATP, 4 mg Stat protein (SUPERDEX 200 eluate for Stat1α and Stat1β; ammonium sulfate pellets dissolved in [20 mM Tris /HCl, pH 8.0] for Stat1tc), 10 μl 1M $MnCl_2$ and $dH_2O$ to 1 ml. The reaction was allowed to proceed for 15 hours at 4° C. After 3 hours an additional 15 μl of 0.1 M ATP was added.

Separation of Phosphorylated from Unphosphorylated Stat Proteins

The in vitro kinase reaction mixture (see above) was freed from EGF-receptor bound to agarose beads by spinning through a plug of siliconized glass wool at the bottom of a pierced Eppendorf tube. The glass wool was washed with 0.5 ml HA-buffer (20 mM Tris/HCl, 1 mM EDTA, 2 mM DTT, pH 8.0) and the pooled volumes loaded onto a heparin agarose (Biorad) column (1.5×7 cm). The column was washed with 50 ml HA-buffer, and then the bound Stat proteins were eluted with two consecutive 50 ml volumes of HA-buffer+150 mM KCl and then HA-buffer+400 mM KCl. Unphosphorylated proteins (eluted with 150 mM KCl) were concentrated by ultrafiltration to about 10 mg/ml, flash frozen on dry ice and stored at −70° C. Phosphorylated Stat1α and Stat1β was concentrated to 1 mg/ml. Glycerol was added to 50% (vol/vol) and the material was stored at −20° C. Phosphorylated Stat1tc was brought to a concentration of about 15 mg/ml and run on a SUPERDEX 200 columns under the conditions described above for the native protein. The gel filtered phosphorylated Stat1tc was pooled, concentrated to approximately 20 mg/ml, flash frozen on dry ice and stored at −70° C.

Electrophoretic Mobility Shift Assays (EMSA)

A 12.5 μl reaction volume contained DNA binding buffer (20 mM Hepes/HCl, 4% Ficoll, 40 mM KCl, 10 mM $MgCl_2$, 10 mM $CaCl_2$, 1 mM DTT) radiolabelled DNA (see below) at a final concentration of $1 \times 10^{-10}$ M unless stated otherwise, 50 ng dIdC, 0.2 mg/ml BSA (Boehringer Mannheim), and the indicated amount of purified phosphorylated Stat1. The reaction volume was mixed and then incubated at room temperature. The time necessary to reach equilibrium was assessed by EMSA [(Stone et al., 1991)]. For all DNA fragments tested, equilibrium turned out to be fully established at the earliest timepoint that can be determined by this technique (30 sec). Therefore incubation periods of 5–15 minutes were chosen. Reaction products were loaded onto a 4% polyacrylamide gel (1.5 mm thick) containing 0.25×Tris-borate-EDTA which had been pre-run at 20V/cm for 2 hours at 4° C. Electrophoresis was continued for 60 minutes at 4° C. Gels were dried and exposed to X-ray film and quantitated by a Molecular Dynamics PhosphoImager.

Binding Site Oligonucleotides

Single-stranded oligonucleotides that were purified on the basis of trityl affinity were obtained from The Great American Gene Company (Ransom Hill). Oligonucleotides longer than 30 nucleotides were further purified on 6% sequencing gels and DNA recovered by soak elution and ethanol precipitation. Nucleic acid concentrations were determined by absorbance at 260 nm using the calculated molar extinction coefficient for each oligonucleotide (corrected for the hyperchromic effect). Complementary oligonucleotides at a concentration of 1 pmol/μl were hybridized for 3 hours after thermal denaturation in 5 mM Tris/HCl, 50 mM KCl, 10 mM MgCl$_2$, pH 8.0. One pmol of synthetic duplex molecule was labelled to high specific activity by the Klenow fill-in reaction (0.5 mM dATP (and 0.5 mM dCTP for S1), 100 μCi [α$^{32}$P] dGTP (3000 Ci/mmol; 10 mCi/ml; and [α$^{32}$P] dTTP for S1; Du Pont), 5 Units of Exo-Klenow enzyme (New England Biolabs)) and rendered completely double-stranded with a 0.5 mM dGTP (and 0.5 mM dTTP for SI) cold chase. Unincorporated nucleotides were removed by gel filtration (spin quant columns; Pharnacia) in 10 mM Tris/HCl, 100 mM NaCl, 1 mM EDTA, pH 8.0. Labelled oligonucleotides were stored at 4° C.

The following duplex DNA fragments with protruding 5'-TCC (except for S1 which has 5'-GATC) were used (the core recognition sequence is underlined): cfosWT 5'-dGTA TTCCCGTCAATGCA-3' (SEQ ID NO:9); Ly6 E 5'-dGTA TTCCTGTAAGATCT-3' (SEQ ID NO:10); cfosM67 5'-dGATTTCCCGTAAATCAT-3'(SEQ ID NO:11); SI 5'-dGTTGTTCCGGGAAAAGG-3' (SEQ ID NO:12); 2× cfosWT (10 bp spacing) 5'-dAGTCAG TTCCCGTCAATGCATCAGGTTCCCGTCAATGCAT-3' (SEQ ID NO:13); 2× cfosWT (5 bp spacing) 5'-dAGTCAG TTCCCGTCAATGAGTTCCCGTCAATGCA-3' (SEQ ID NO:14); 2× cfosWT (15 bp spacing) 5'-dAGTCAG TTCCCGTCAATGATCGCTACAGAG TTCCCGTCAAGCA-3' (SEQ ID NO:15); 2× cfosWT (inverted repeat) 5'-dAGTCAT TTCCCGTCAATGCATCAGTTGACGGGAAAGTAGT-3' (SEQ ID NO:16).

Dissociation Rate Determination

Under the reaction conditions described above, each oligonucleotide (at 2×10$^{-9}$ M or otherwise stated) was mixed with 0.55×10$^{-9}$ M dimer of purified phosphorylated Stat1 protein. The reaction volume was scaled up to 100 μl. The reaction was incubated for 5–15 min at room temperature and for time zero, an aliquot (10 μl) was removed and loaded directly onto a pre-run polyacrylamide gel (see above). Afterwards, a 100×molar excess of homologous unlabelled DNA (in less than 1% of the reaction volume) was added. At subsequent time points (indicated in FIGS. 5C–5D, and 7) 10 μl aliquots were withdrawn and also loaded onto the running gel (at 10 V/cm). After entering the final time point (after 30–45 min), electrophoresis was continued at 20 V/cm until the unbound labelled DNA-fraction reached the bottom of the gel. Gels were dried, exposed to X-ray film and labelled protein/DNA complexes and unbound labelled DNA were quantitated as described above. The half life was determined from a semi-log plot of the numerical data (shifted radioactivity over shifted radioactivity at time zero versus time). For many sequences studied, the half life was too short (>30 sec) to be determined by EMSA. All experiments were performed at least twice with the different oligonucleotides.

Determination of Apparent Equilibrium Constants for Protein DNA interactions

A fixed quantity of $^{32}$P labelled oligonucleotide varied between 1×10$^{-10}$ M and 5.6×10$^{-10}$ M in three separate experiments, was titrated against a standard protein dilution series (common to all oligonucleotides tested) in a volume of 12.5 μl under the reaction conditions described above. Numerical data were used to construct a standard binding curve from which the free dimer concentration, when 50% of the probe is shifted, could be determined.

Results

Production by Recombinant Techniques and Purification of Stat1 cDNA encoding Stat1α or Stat1β was inserted in baculovirus transfer vector (pAcSG2) and co-transfected with modified linearized AcPNV baculovirus DNA to produce virus particles. Insect cells (Sf9 cells) infected with the respective recombinant baculovirus produced a 91 kDa protein and a 84 kDa protein that could be identified with an antibody raised against Stat1 by Western blot analysis. These proteins were purified (FIG. 1A) through the steps indicated in Table 1.

TABLE I

Purification of Stat 1α/β

| STEP | | VOLUME (ml) | PROTEIN (mg) |
|---|---|---|---|
| I | Crude Extract[a] | 80 | 550[b] |
| II | S-SEPHAROSE | 120 | 30[b] |
| III | Q-SEPHAROSE | 30 | 12[b] |
| IV | Ammonium Sulfate | 1 | 8[b] |
| V | Alkylation | 10 | 8[b] |
| VI | Phenyl-SEPHAROSE | 25 | 6[c] |
| VII | SUPERDEX | 3 | 5[c] |

[a]Following precipitation at pH 6.2 from 5 × 10$^8$ cells.
[b]Protein concentrations were determined by the method of a dye-binding assay (Bradford, 1976) using bovine serum albumin as the protein standard.
[c]Protein determined by ultraviolet light absorbance as described in METHODS.

Stat1α is 750 amino acids long. Stat1β is a product of a differentially spliced mRNA which encodes a protein 712 amino acids long (Schindler et al., 1992; Yan et al., 1995). It is known that both Stat1α and 1β can be phosphorylated on a single tyrosine, residue 701. In vivo, both forms of the protein dimerize upon phosphorylation, and then translocate to the nucleus to bind specific DNA sites (Shuai et al., 1992; Shuai et al., 1993a).

Figure 1B:
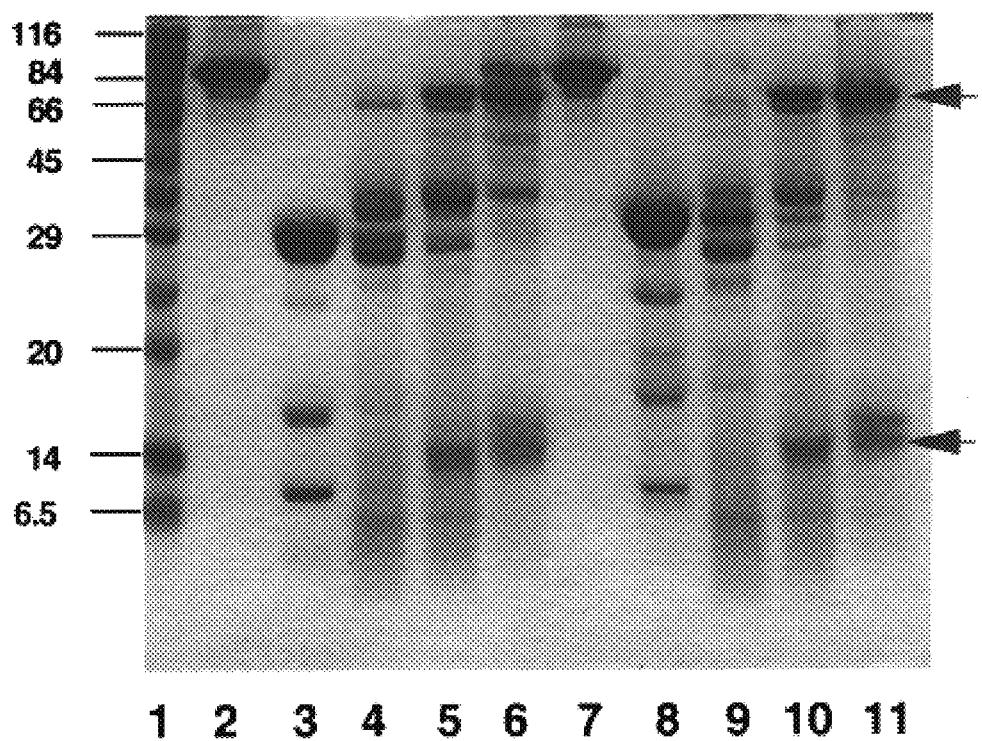
FIG. 1B. Proteolysis of human Stat1α. 40 μg of purified Stat1α were digested with various amounts of subtilisin (lanes 4–6) or proteinase K (lanes 9–11) for 30 min on ice (as described in Materials and Methods, infra). The ratios (wt/wt) of protease to protein were 1:8 (lanes 4 and 9), 1:80 (lanes 5 and 10), and 1:800 (lanes 6 and 11). Aliquots of the reactions were resolved on a 16.5% SDS-polyacrylamide gel followed by Coomassie staining. Lane 1, molecular weight standards in kDa; lanes 2 and 7, untreated Stat1α; lane 3, subtilisin (15 μg); lane 8, proteinase K (15 μg). Stable fragments of 65 kDa and 16 kDa (see text) are marked with arrows.

The purified Stat1α was digested with several proteolytic enzymes to determine whether the protein could be divided into functional domains. Both subtilisin and proteinase K produced two major digestion products (FIG. 1B), the largest of which migrated on SDS polyacrylamide gel electrophoresis with an estimated size of 65 kDa, as compared with the full length protein of 91 kDa. (Cleavage products of approximately 40 and 30 kDa were also seen). The 65 kDa product had an N-terminal sequence of XTVMLDKQEKE indicating that it resulted from cleavage between residues 131 and 132 of the full length protein. A single prominent smaller fragment of about 16 kDa was also observed. This fragment was the only one generated that retained reactivity with an antibody raised against the amino terminus of Stat1. The shorter 16 kDa fragment was therefore identified as an N-terminal fragment of the molecule.

The major proteolytic cleavage fragment, which was also the longest, began at residue 132. This fragment was poorly recognized by an antibody to the carboxyl terminal 38 amino acids of Stat1α which indicated an additional cleavage near the carboxyl terminus. A bacterial expression clone encoding residues 132–713 was prepared since this fragment was shown to be resistant to further proteolysis (above), and Stat1β, which terminates at residue 712, is known to be active form of the protein in vivo. The product, Stat1 (132–713) or Stat1tc, was expressed in relatively large quantities in E. coli and a major fraction of the protein proved to be soluble. Stat1tc was purified to homogeneity (FIG. 1A and as in the Materials and Methods, above). The recombinant truncated Stat protein of the present invention appears to be a unique form of Stat protein, since the Stat fragments listed in Table II were found to essentially accumulate entirely in inclusion bodies.

TABLE II

Solubility of Recombinant Stat 1 Fragments

| AMINO TERMINUS | CARBOXYL TERMINUS | SOLUBLE |
|---|---|---|
| 132 | 713 | YES |
| 200 | 713 | NO |
| 250 | 713 | NO |
| 300 | 713 | NO |
| 370 | 713 | NO |
| 420 | 713 | NO |

The expression vectors for the nucleic acids coding the amino acid sequences for the protein fragments of Stat1, listed above, were constructed and expressed as described in the METHODS for the truncated protein Stat1, Stat1tc. The sequences are based on the Stat1α as described above. The positive (YES) denotation for being soluble, is indicative of significant quantities of the corresponding protein fragment being free of the inclusion bodies. As can be seen from the table, only the truncated Stat protein present invention (132–713) was found to occur free of inclusion bodies in significant quantities.

Aggregation of Native Proteins

It appeared possible that aggregation of the protein occurred since purified Stat1α, Stat1β and Stat1tc eluted in peaks with broad leading shoulders, during gel filtration. Thiol crosslinking was suspected as the cause, since the preparation had aggregates that migrated with an apparent molecular mass corresponding to dimers and higher order oligomers when run under non-reducing conditions on a denaturing polyacrylamide gel (not shown). Accordingly, to block the reactive thiols, the cell extracts (from baculovirus infected Sf9 cells for Stat1α and transformed E. coli for Stat1tc) were incubated with N-ethyl maleimide (NEM) to test if the modification of the cysteine residues: (1) could prevent the aggregation, and (2) whether such modification would lead to a non-aggregated protein preparation that retained its functional properties. The procedure worked unexpectedly well and this alkylation step became part of the purification procedure (Table 1).

The purified protein was cleaved with cyanogen bromide and Endoprotease Asp-N. Mass spectrometric analysis of the resulting peptides showed that cysteines 155, 440, and 492 were alkylated by the NEM treatment, whereas two other cysteines were not (Cys 552 and Cys 577). The NEM treatment did not affect any of the subsequent experiments (e.g., DNA binding, see FIG. 3B) and was adopted as the standard preparation of a homogeneous protein.

In vitro Phosphorylation of Stat1α, Stat1β and Truncated Stat1 by the EGF-receptor The in vivo activated DNA binding form of Stat1 is phosphorylated on tyrosine 701 when isolated from mammalian cells treated with ligands that activate either JAK kinases or transmembrane receptor kinases (Shuai et al., 1992; Shuai et al., 1993b). EGF-receptor kinase activity was achieved with immunoprecipitates of membrane preparations from cultured human A431 cells that express $5 \times 10^6$ EGF-receptors per cell (Yarden et al., 1985; Quelle et al., 1995). These membrane preparations were used as the source of enzyme to catalyze the tyrosine phosphorylation of Stat1 and the truncated Stat1.

Figure 2A:
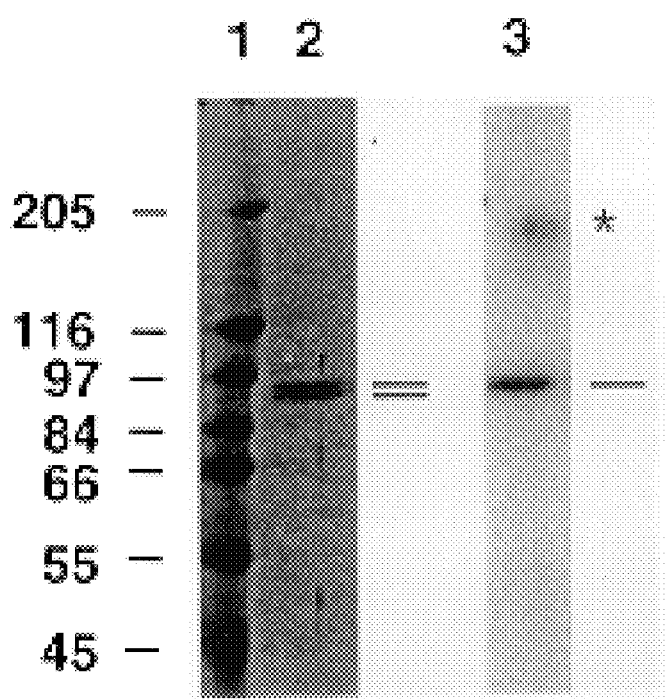
FIG. 2A. Phosphorylation of Stat1α with EGF-receptor kinase in vitro. 2 μg of Stat protein was incubated with EGF-receptor and 1 μCi of $^{32}P$ γATP for 6 h at 4° C. The reaction (20 μl volume) was stopped by the addition of SDS-sample buffer, resolved on a 7% SDS-PAGE, which was subsequently dried and exposed to an X-ray film. The typical doublet pattern for phosphorylated Stat1 (Shuai et al., 1992) is seen in the Coomassie stained gel in lane 2. Lane 3 shows the corresponding autoradiogram. Only the slower migrating band contains $^{32}P$. (*) denotes the position of the phosphorylated EGF-receptor. Fast and slow migrating Stat proteins are pointed out with lines. Lane 1 contains the molecular weight markers and their respective molecular weights are denoted in kDa.

As detailed above, in vivo, Stat1α is phosphorylated on a specific tyrosine residue (Tyr701). The resulting phosphorylated form of the protein runs at a slightly slower rate during polyacrylamide gel electrophoresis, in comparison to the nonphosphorylated form (Shuai et al., 1992). This same change in mobility was observed after purified Stat1α was treated in vitro with EGF-receptor kinase preparations. In addition, when the enzymatic reaction was carried out in the presence of $^{32}P\gamma ATP$, the slower running protein was found to contain $^{32}P$ (FIG. 2A). Similar results were obtained for the in vitro phosphorylation of Stat1tc. However, it was clear that not all of the Stat1 protein was phosphorylated (FIG. 2A). Although subsequent experiments yielded somewhat higher amounts of phosphorylation, the percentage of Stat protein that was phosphorylated never exceeded 75%.

Figure 2B:
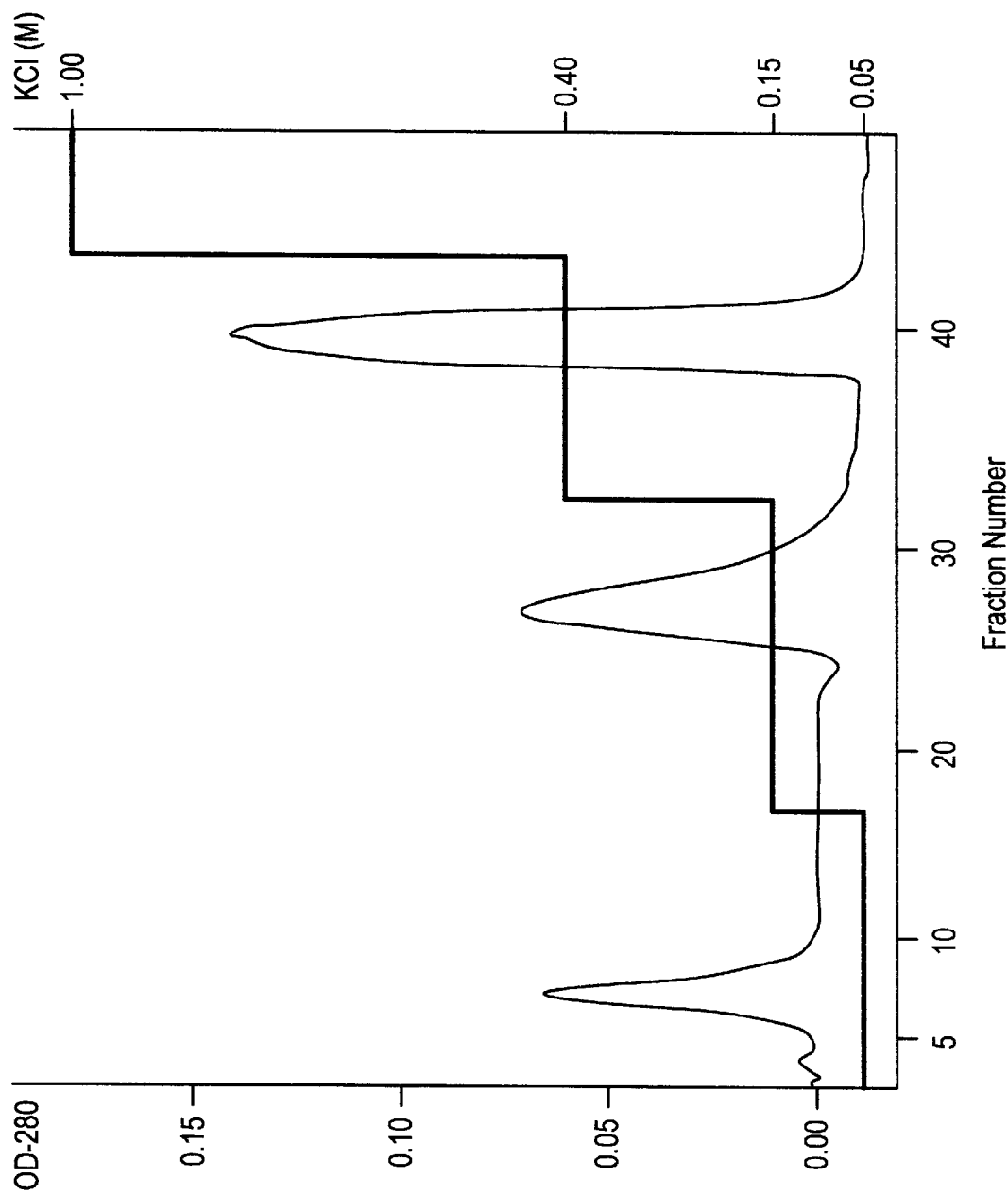
FIGS. 2B–2D Isolation of in vitro phosphorylated Stat1tc. A total of 25 mg of protein was loaded on a heparin agarose column after an in vitro phosphorylation reaction and removal of EGF-receptor (see Materials and Methods). Depicted is the column profile of UV-absorptive material eluted with successive steps of 50 mM KCl, 150 mM KCl,and 400 mM KCl. Five microliters of the indicated fractions (2.5 ml) were resolved by 7% SDS PAGE and stained with Coomassie blue (lower insert) or blotted on a nitrocellulose membrane and probed with an anti-phosphotyrosine-antibody (1:1500 diluted PY 20 (UBI); upper insert). Molecular weights are denoted in kDa.
Figure 2C:
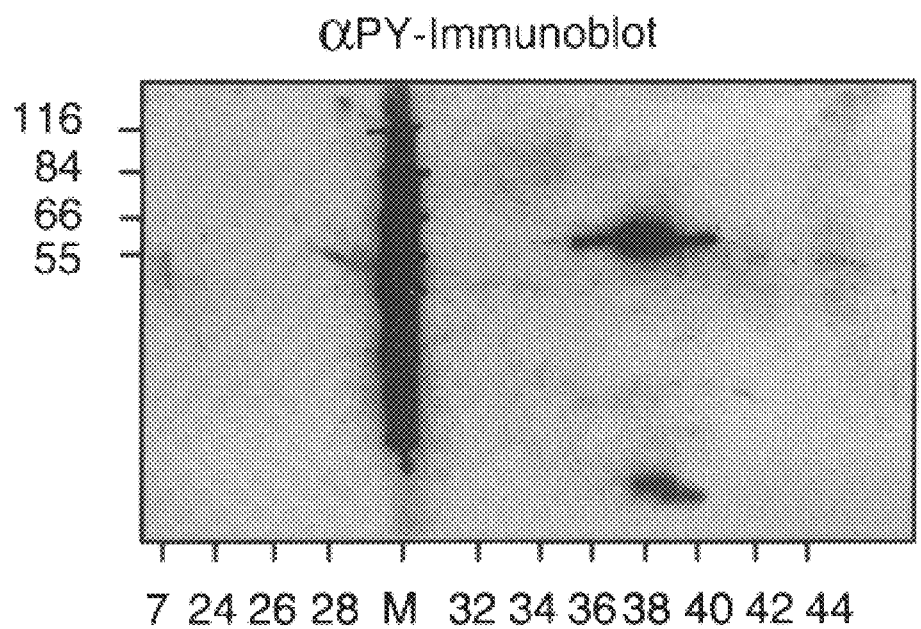
Figure 2D:
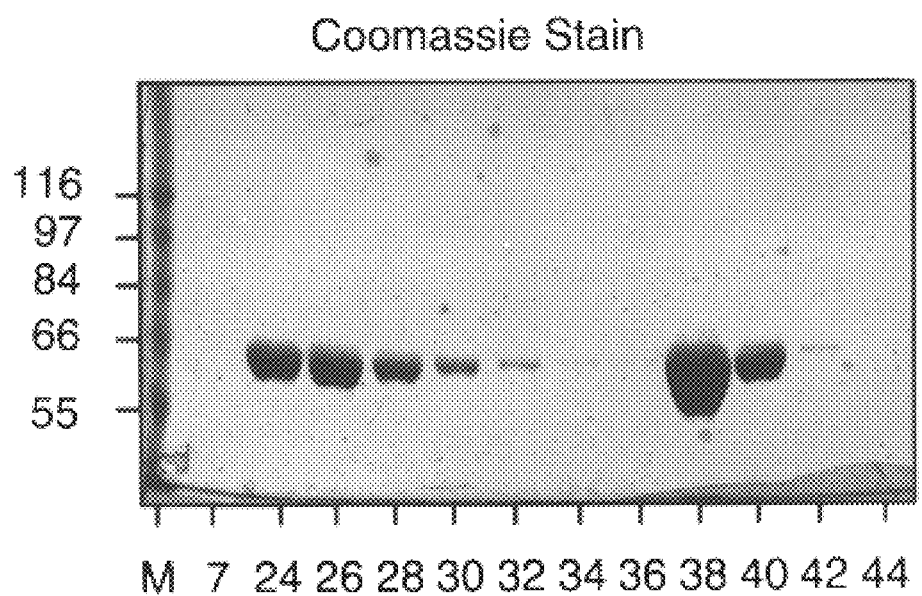

Therefore a method of separating phosphorylated from nonphosphorylated Stat protein was required. Although the phosphorylated protein forms a dimer, this dimer elutes in a peak strongly overlapping the elution peak of the corresponding nonphosphorylated monomer. Therefore, alternative means was required. After many unsuccessful attempts using various chromatography procedures, step-wise elution of the protein mixture bound to heparin agarose proved surprisingly successful (FIG. 2B–2D). This novel procedure resulted in a separation of two peaks containing Stat proteins (eluted in steps of 150 mM and 400 mM KCl). The tyrosine phosphorylated protein (FIG. 2B–2D) which, in addition, had DNA binding activity, was present in the second of these two chromatographic peaks.

Figure 2E:
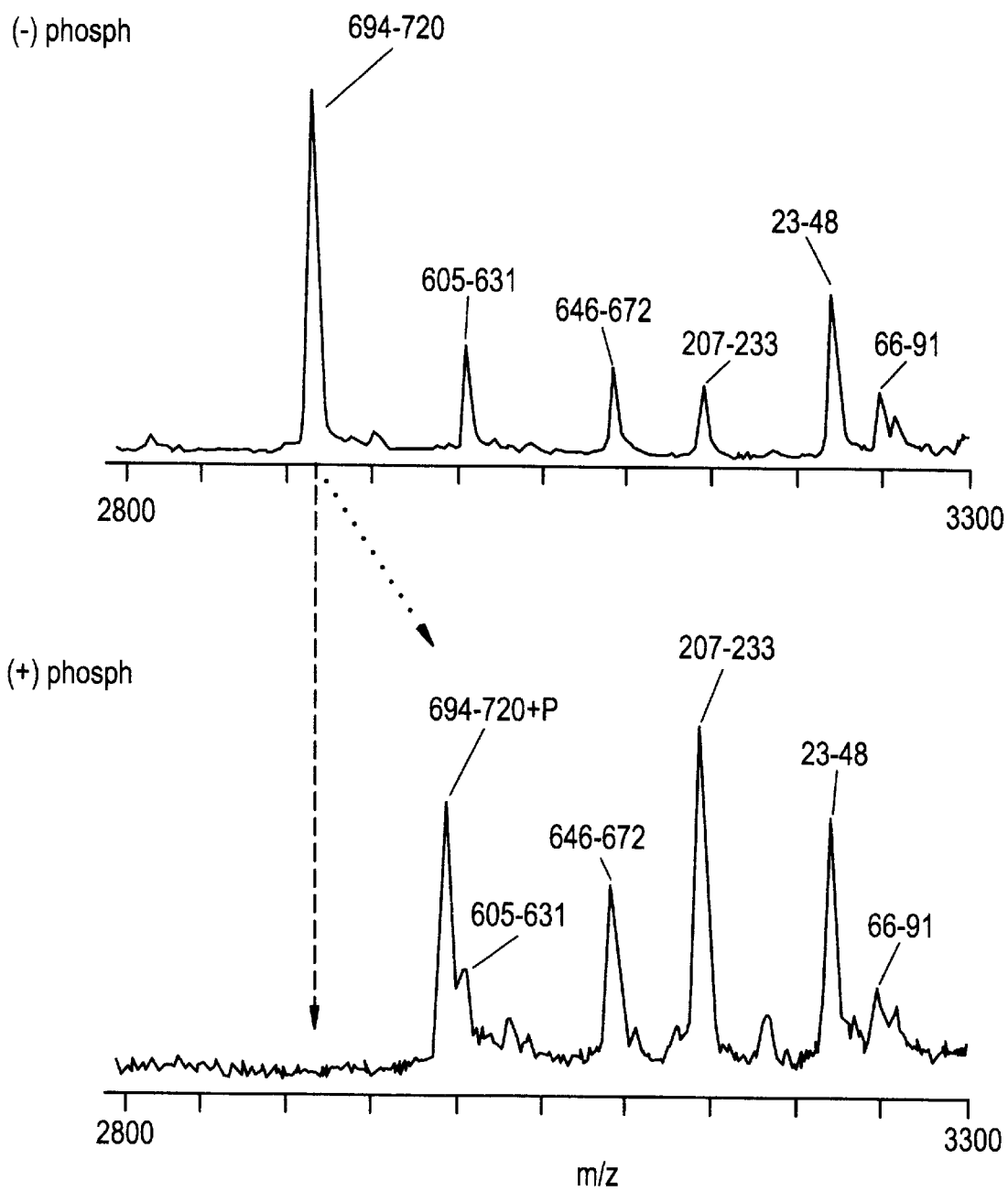
FIG. 2E. Tyrosine 701 is phosphorylated by EGF-receptor. The endoproteinase AspN digests (15 min) were carried out on alkylated Stat1β in either the unphosphorylated form (– phosph, upper half) or the chromatographically purified phosphorylated form (+ phosph, lower half). The relevant proteins of the matrix-assisted laser desorption/ ionization mass spectrum are shown. Accurate molecular mass determinations allowed for unequivocal identification of the peptide fragments. Peaks are labeled according to the amino acid sequence of the corresponding peptides.

To determine the purity of the isolated material and to analyze whether the correct tyrosine residue was phosphorylated, both purified, unphosphorylated (i.e., protein not reacted with EGF-receptor) and phosphorylated protein (i.e., protein obtained from the chromatographic peak containing phosphotyrosine from the heparin agarose column described above) were subjected to Endoprotease Asp-N digestion and the resulting peptide fragments analyzed by mass spectrometry (FIG. 2E). Phosphorylation increases the molecular mass of an unphosphorylated fragment by 80 daltons, that is, comparison of the Asp-N fragments of phosphorylated versus unphosphorylated Stat's showed an 80 dalton shift of the fragment 694–720 (FIG. 2E), demonstrating that in vitro phosphorylation by EGF-receptor kinase occurred exclusively on the single tyrosine residue that is phosphorylated in the cell. In addition, the bottom panel of FIG. 2E demonstrates the absence of unphosphorylated Tyr 701 in the purified EGF-receptor kinase-treated protein.

Both In vitro Phosphorylated Stat1α and Stat1tc Bind Specific DNA Fragments

Figure 3A:
FIG. 3A. DNA binding of purified phosphorylated Stat1α (lane 1) and Stat1tc (lane 2) using as a probe the radioactively labelled cfosWT sequence. Binding reactions contained equimolar amounts of the respective proteins. The position of migration of the free DNA probe (free) and the protein/DNA complex (bound) is indicated. Note the presence of a slower migrating band only with the full length Stat1α, lane 1 (see also FIG. 3B).
Figure 3B:
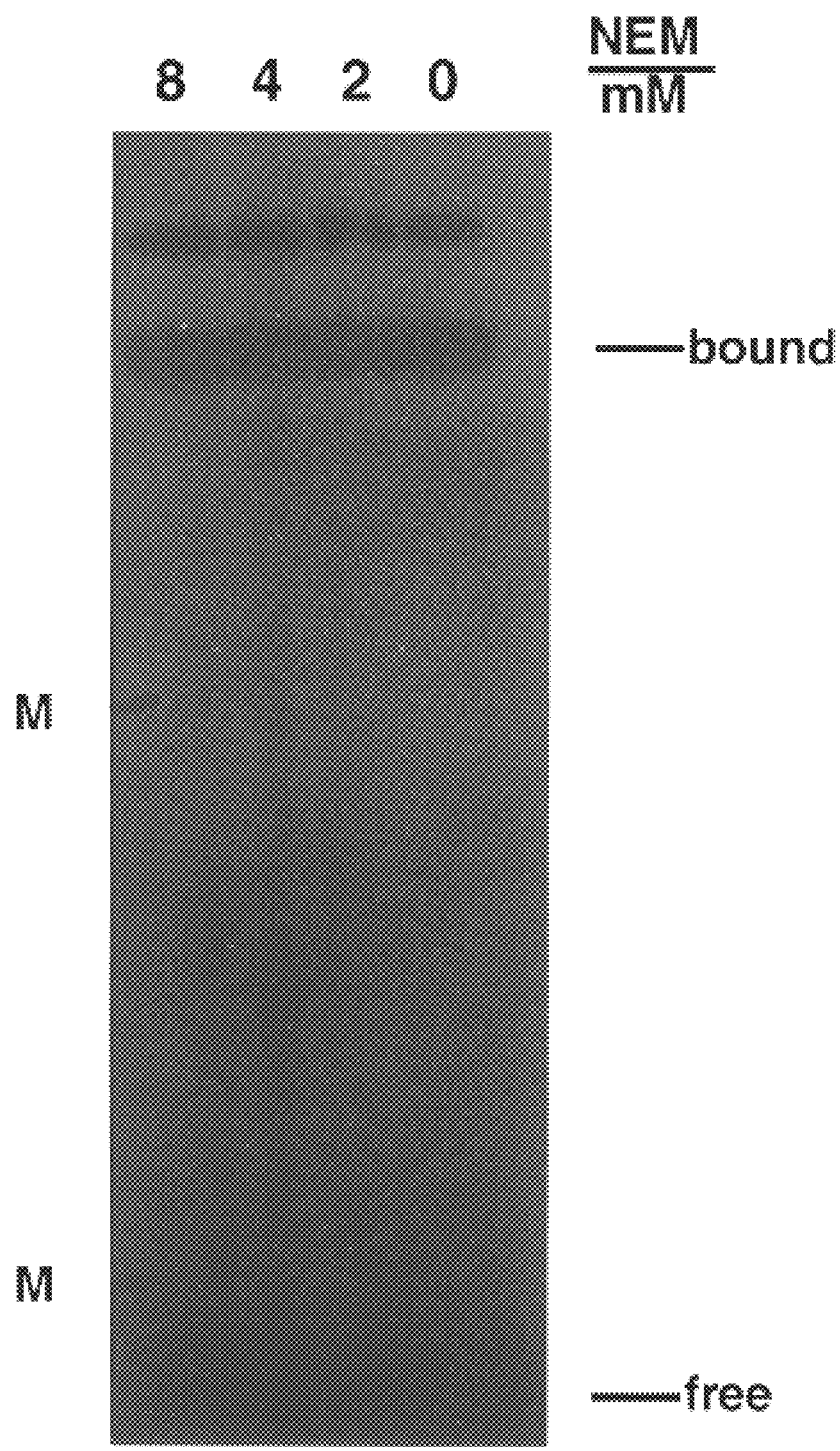
FIG. 3B. Influence of cysteine alkylation on the DNA binding activity of Stat1α. A mixture of phosphorylated and unphosphorylated protein (0.23 µM final; ~15% phosphoprotein) was reacted in the presence of 0.8 mM DTT and the indicated concentrations of N-ethyl-maleimide (NEM) for 20 min at room temperature in a volume of 12.5 µl. The reaction was stopped with DTT (final concentration of 10 mM) followed by the addition of 1.5 pmoles of labelled probe (cfosM67). Samples were resolved on a 4.5% native polyacrylamide gel. (M) denotes the position of bromophenol blue (lower) and xylene cyanol (upper) markers.

Electrophoretic mobility shift assays (EMSA) (Fried and Crothers, 1981; Garner and Revzin, 1981) were used to test DNA binding of tyrosine phosphorylated Stat1α and Stat1tc. Both proteins were found to bind to all tested labelled deoxyoligonucleotides known from earlier studies to bind Stat1 (the oligo cfosWT is illustrated in FIG. 3A). The bound complexes were not affected by N-ethyl maleimide indicating that alkylation of cysteine does not affect DNA binding (FIG. 3B). This result is consistent with earlier experiments showing that ISGF3α, now known to be a Stat1:2 heterodimer, is not affected by NEM treatment (Levy et al., 1989). In addition, the DNA binding ability of homodimeric phosphorylated Stat1α or its truncated form was highly resistant to up to 2 Molar monovalent salt concentrations.

Strength of Stat1 Binding to DNA and Estimation of Dissociation Rates

We next used the EMSA assay to obtain an estimate of the binding affinity of Stat1α and Stat1tc to DNA. Both forms of the protein behaved identically when using a fixed amount of deoxyoligonucleotide and increasing protein concentrations (FIGS. 4A and 4B). A $K_{eq}$ of approximately $1 \times 10^{-9}$ M was estimated from this data for both proteins when the bound and unbound fraction of DNA was compared as a function of protein concentration. This is in the affinity range for transcription factors in general which have been reported to have a $K_{eq}$ between $10^{-9}$ and $10^{-12}$ M for proteins with the highest affinity for their cognate DNA sites (Riggs et al., 1970; Affolter et al., 1990). The same results were obtained with several different oligonucleotides, the Ly6E and cfosWT Stat binding sites, which are "weak" binding sites, and "strong" sites, such as the selected optimum site, S1 (Horvath et al., 1995) and a mutated cfos sequence (M67 site; Wagner et al., 1990). ["Strong" and "weak" in this context refer to experiments with cell extracts containing activated Stat1 which binds more of some oligonucleotides (strong) than others (weak).]

The stability of preformed DNA protein complexes were examined by the following method: the formation of a complex between protein and labelled oligonucleotides is allowed to occur and unlabelled oligonucleotides are added in vast molar excess after the reaction reaches equilibrium. At various times after the addition of unlabelled competitor DNA, aliquots are layered on a running native polyacrylamide gel to determine free and bound oligonucleotides. This type of experiment was carried out with both Stat1α, and Stat1tc, and with two different labelled DNAs, the natural cfos site, an example of a "weak" site, and the mutated cfos-promotor element (M67) an example of a "strong" site.

With the "weak" site, the "off" time was so short that the addition of unlabelled nucleotides for as little as 30 seconds removed all preformed protein DNA complexes (FIG. 5C, Stat1α shown in the left panel). With the "strong" site, the preformed labelled complexes were displaced more slowly, the t½ is estimated to be 3 minutes (FIG. 5B, right panel employed Stat1tc). In these experiments there was no difference between Stat1α and Stat1tc.

Stat Binding to Tandem DNA sites: Evidence for Stabilized Promotor Occupancy through Protein:Protein Interactions of Stat1α and Stat1β Versus Stat1tc Two recent reports on promoters of genes dependent for transcription on Stat proteins have indicated that two neighboring Stat binding sites are required for maximal transcriptional stimulation. In one of these reports the human mig gene promoter was found to have two weak Stat1 binding sites within 25 bp, neither of which alone conferred IFN-γ transcriptional activation while both sites together did so. Moreover the active element formed complexes with Stat1 protein that migrated more slowly than Stat1 dimers bound to DNA. The authors suggested that interaction between Stat homodimers might occur in the complexes (Guyer et al., 1995). In addition, we recently reported two D-Stat binding sites were found in the segment of the even-skipped promoter that directs stripe 3 formation in Drosophila embryos; both sites were required for maximum stripe 3 expression (Yan et al., 1996).

With the present demonstration that Stat1α protein indeed does have such a rapid off-time, especially on natural "weak" binding sites, the binding of activated protein to oligonucleotides containing two weak DNA binding sites was investigated. The experiments were carried out with both Stat1α and Stat1tc and a labelled oligonucleotide containing a variety of arrangements of two "weak" binding sites. With two binding sites present in tandem on the same DNA fragment and at a moderately high concentration of protein ($0.55 \times 10^{-9}$ M), Stat1α and Stat1tc each formed both a homodimer complex and an additional complex that migrated more slowly [2× (dimeric)]. The mobility of this slower moving complex suggested occupation of both DNA binding sites, indicating one DNA molecule with two Stat dimers bound to it (FIG. 6A, time zero). When such complexes were challenged for various times with an excess of unlabelled oligonucleotide, both the dimeric and [2× (dimeric)] complexes were dispelled but with different kinetics for Stat1α and Stat1tc. The Stat1tc showed almost immediate displacement (less than one minute) of both dimeric and [2× (dimeric)] complexes (FIG. 6A, left). In contrast, whereas as anticipated, the Stat1α homodimer also disappeared quickly, the [2× (dimeric)] complex required more than 30 min for partial displacement, indicating a significant increase in stability of this larger complex with the full length proteins.

Figure 6B:
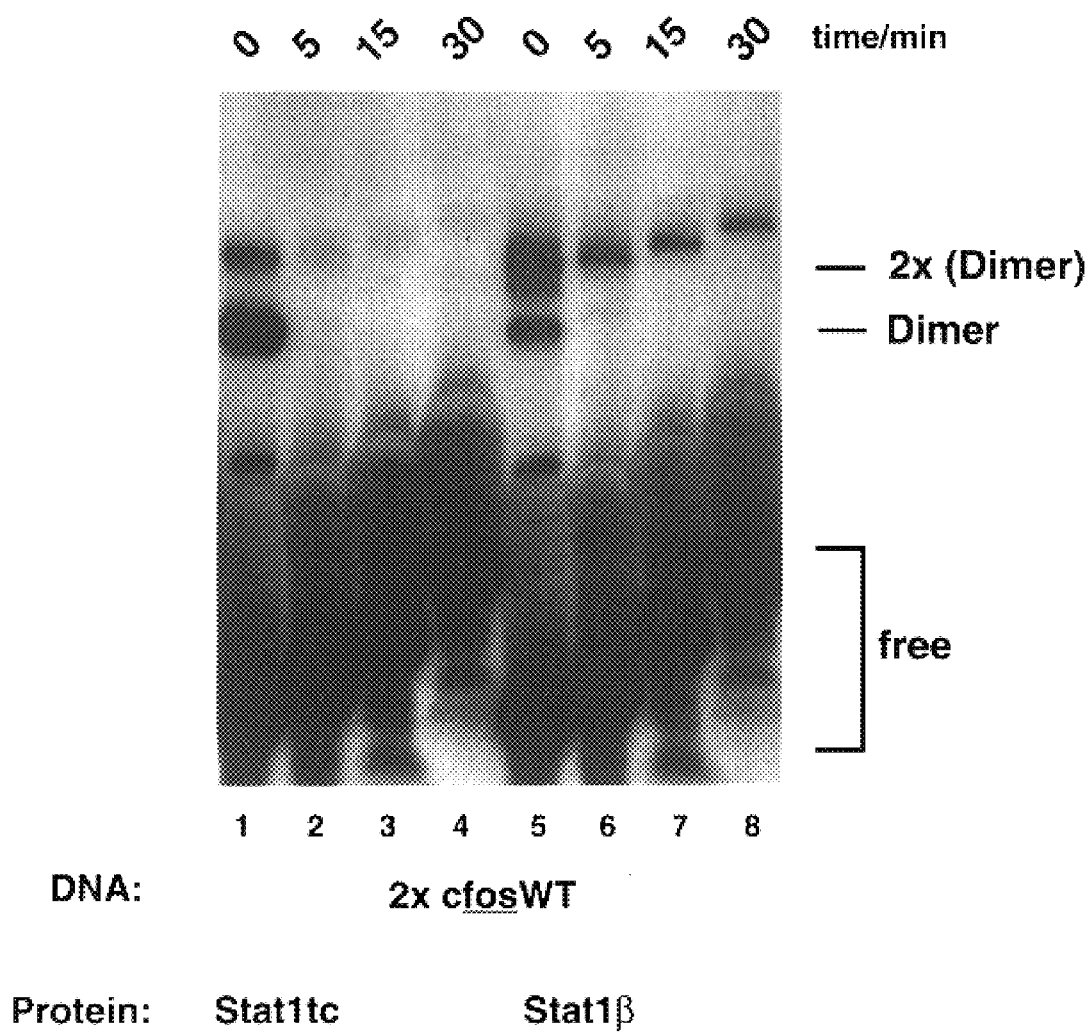
FIG. 6B. Identification of the amino terminal 131 amino acids as functional in (2×(Dimer)) stabilization on DNA. Comparison of stability of Stat1β (lanes 5–8) and Stat1tc (lanes 1–4) on DNA fragments containing two consecutive binding sites (2× cfosWT, 10 bp apart). The experimental protocol was the same as in FIG. 6A.

These results suggested that when Stat1α is bound at tandem binding sites, protein:protein interactions occur that require the presence of the amino and/or carboxyl terminal domain of Stat1α to form the more stable DNA:protein complexes. To examine this question we compared Stat1tc in the chase assay with the Stat1β protein, which only lacks the C-terminal domain. As shown in FIG. 6B, Stat1β exhibits the same behavior as the full length protein, indicating involvement solely of the amino terminal region (between amino acids 1 and 131) in stabilizing the [2× (dimeric)] complexes.

Figure 7A:
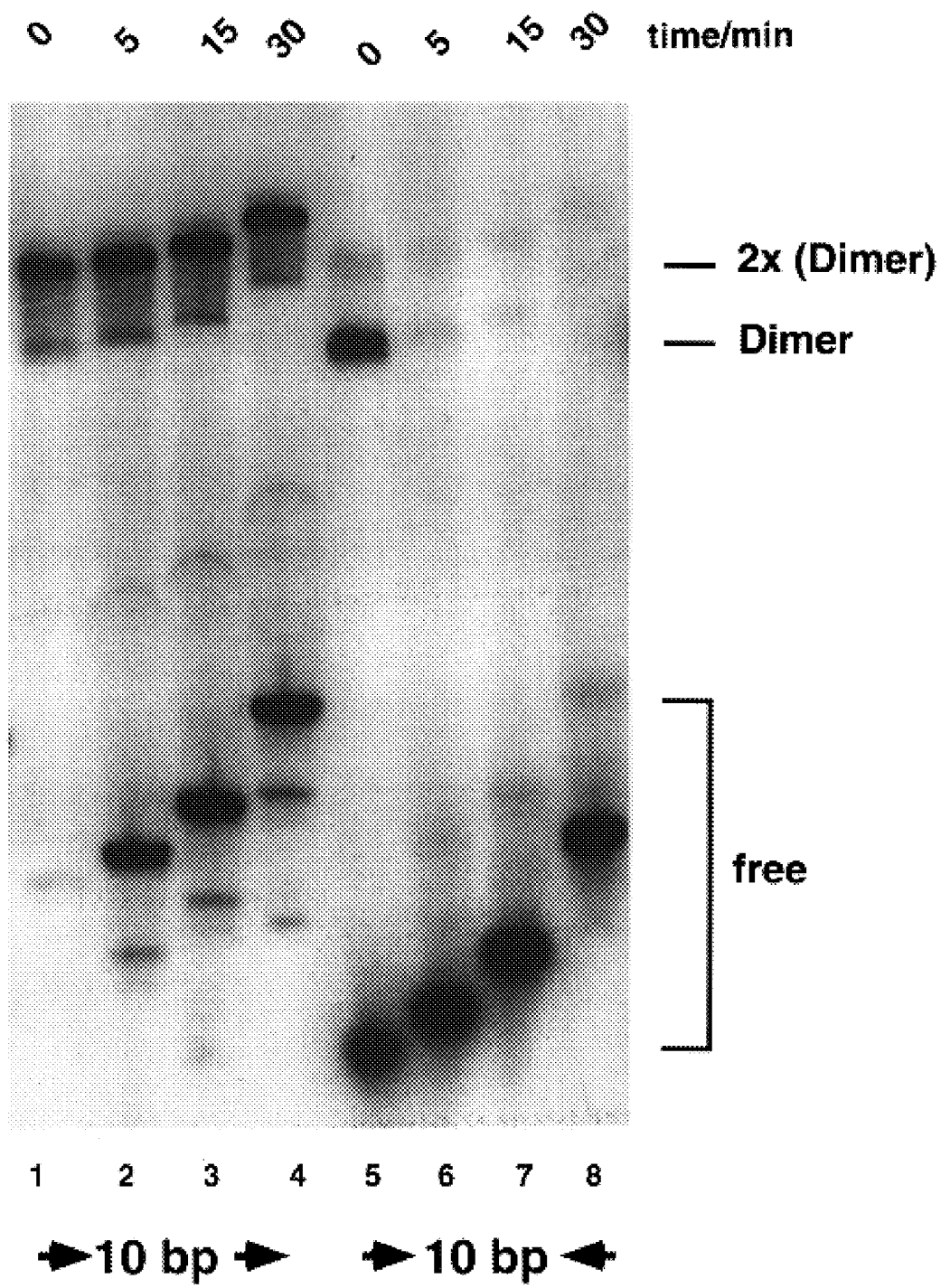
FIG. 7A. Influence of promotor orientation on protein/DNA complex formation and stability. $1.65 \times 10^{-9}$ M Stat1α dimer were equilibrated with labelled DNA ($0.7 \times 10^{-9}$ M) with two consecutive binding sites (2× cfosWT) 10 bp apart in parallel (lanes 1–4) or antiparallel (lanes 5–8) orientation. The preformed complexes were chased with unlabelled competitor DNA as described in the legend to FIG. 6A.

We then tested the importance of the orientation and the spacing of the two Stat binding sites within the synthetic oligonucleotides. First the DNA sites that exhibited stabilization in [2× (dimeric)] binding were changed from tandem (→→) to inverted (→←), keeping the spacing at 10 basepairs (bp) between the two binding sites. While both oligonucleotides were capable of binding two dimers (with the tandem binding sites in inverted orientation showing much less of the [2× (dimeric)] complex even at relatively high protein to DNA ratio), the inverted sites showed no increased stability when challenged with unlabelled oligonucleotide (FIG. 7A).

Figure 7B:
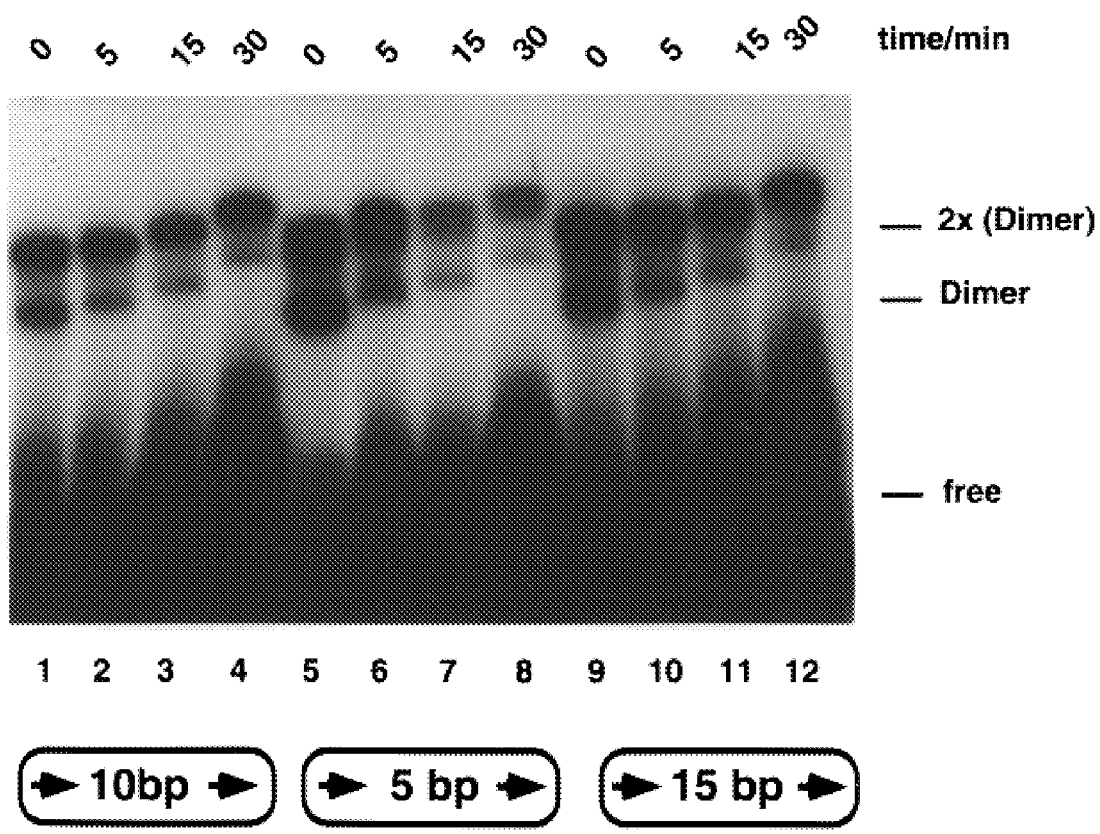
FIG. 7B. Stat1α binding to DNA fragments with two parallel binding sites (2× cfosWT) spaced 10 bp (lanes 1–4), 5 bp (lanes 5–8), or 15 bp (lanes 9–12). The chase experiment was performed as described in the legend to FIG. 6A.

Oligonucleotides with tandem binding sites spaced by 5 or 15 bp were prepared to compare with the original oligonucleotide with 10 bp spacing. The oligonucleotide with a 15 bp spacing behaved indistinguishably from the one with 10 bp spacing, while the oligonucleotide with 5 bp spacing showed much less evidence of enhanced stability of the [2× (dimeric)] complex, suggesting that protein:protein interaction was less likely when the DNA spacer was of inadequate length (FIG. 7B).

Discussion

The production of three purified Stat1 protein preparations from recombinant DNA constructs was achieved: Stat1α and Stat1β from baculovirus infected insect cells, and a Stat1tc from *E. coli*. Digestion of purified Stat1α protein suggested a compact domain in the amino terminus of 131 amino acids and a relatively protease-resistant large carboxyl terminal fragment (132–712). Activated EGF-receptor partially purified from membranes by immunoprecipitation was capable of in vitro catalysis of the phosphorylation of tyrosine 701, of Stat1α, Stat1β, and Stat1tc. This is the same tyrosine that is phosphorylated in vivo by either IFN-α, IFN-γ or EGF treatment of cells (Shuai et al., 1992; Shuai et al., 1993a). This in vitro approach was more efficient in generating activated Stat1 molecules than previous attempts that employed either co-infection of Stat1 and a JAK kinase in the baculovirus/insect cell system in vivo, or in vitro kinase assays with JAK kinases [unpublished observations and (Yan H. et al., 1996)]. These results on in vitro phosphorylation of the protein plus alkylation to prevent aggregation, coupled with an adequate chromatographic protocol, allowed the purification of milligram quantities of activated protein. These techniques are also be applicable to other Stat molecules such as Stat 2, 3, 4, 5A, 5B, and 6.

Analysis of the peptides derived from the purified phosphorylated protein by mass spectrometry, did not reveal significant contamination with unreacted Stat monomers. All three tyrosine-phosphorylated Stat1 derivatives dimerized and, as tested by EMSA, bound to the same DNA oligonucleotides previously shown to bind activated Stat1 in cell extracts.

The structure of the Stat protein is expected to be complex considering the number of interactions these proteins must undergo. The region from residues 400–500 specifies DNA contacts (Horvath et al., 1995), while the carboxyl terminal half of the molecule contains the recognizable SH2 and putative SH3 domains (Fu, 1992; Schindler et al., 1992), and the carboxyl terminus comprises the transactivation domain (Muller et al., 1993; Wen et al., 1995). From the digestion by proteases which released an amino terminal and a carboxyl terminal fragment a compact structure for the amino terminal of about 131 amino acids, is indicated. In addition there is a large stable fragment beginning at amino acid 132 that can be phosphorylated on a specific tyrosine and dimerize. The Stat1 protein binds to various DNA fragments with a $K_{eq}$ of $1 \times 10^{-9}$ M. Compared to other regulatory proteins this is a relatively modest affinity. Despite having similar apparent $K_{eq}$ values, the binding with DNA may differ significantly in rates of association with and dissociation from the Stat protein. The Stat1 protein achieves equilibrium in DNA binding very rapidly, far quicker (less than 30 seconds) than the EMSA technique can determine. When the stability of Stat1 protein preparations to the various Stat1 binding sites were examined, measurable differences became apparent. Although the protein/DNA complex had a half life of no more than 3 minutes for any of the sites tested, the "off" times for different oligonucleotides varied by at least six-fold. The difference between "strong" and "weak" oligonucleotide binding as detected in gel shift assays was found to be due to the rapid "off" time in competition assays with the displacement from "weak" sites being essentially instantaneous. Regarding the DNA binding activities of the Stat dimer to a single recognition sequence, no differences between the full length Stat1α and the carboxyl- and amino terminally truncated Stat1tc was observed.

The new finding of great potential biological relevance in these studies concerns the cooperative stabilization of Stat homodimers on neighboring binding sites. This was observed when two tandem sites (separated by 10 or 15 bp) were both occupied by homodimers. A large complex was formed consisting presumably of two homodimers which was more stable to competition with unlabelled oligonucleotides than one dimer binding to a single site. This interaction required a minimum spacing (greater than 5 basepairs) between adjacent sites and was strongly orientation-dependent, i.e., it occurred only if both recognition sequences were in tandem.

Additionally a domain in the Stat1 molecule required for this dimer:dimer interaction was determined. The Stat1β lacking the carboxyl terminal 38 amino acids showed the same stabilization of the [2× (dimeric)] Stat complex on the DNA as the full length protein. However, the truncated protein Stat1tc that lacks the amino terminal 131 amino acids (as well as the carboxyl terminal sequence) formed the higher order complex less well, and this complex was not stabilized during oligonucleotide competition. Thus the amino terminal 131 amino acids of Stat1 defined by proteolysis as a stable domain, and which is dispensable for dimer formation and binding to single DNA sites, participates in Stat dimer:dimer interaction on tandem DNA sites. Interestingly, the isolated amino terminal domain dimerizes in solution. The amino terminus of the Stats shows rather high sequence homology (Schindler and Darnell, 1995), indicating that protein:protein interaction in this domain is of general importance in Stat function. Since there is evidence from the mig-gene (Guyer et al., 1995) that neighboring "weak" Stat binding sites are required for a IFN-γ response, it indicates that the interaction we describe has a biological role.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

References

Affolter, M., Percival-Smith, A., Muller, M., Leupin, W., and Gehring, W. J. (1990). DNA binding properties of the purified Antennapedia homeodomain. *Proc. Natl. Acad. Sci. USA* 87, 4093–4097.

Bradford, M. M. (1976). A rapid and sensitive method for quantification of microgram quantities of protein utilizing the principle of protein-dye binding. *Anal. Biochem.* 72, 248–251.

Cantor, C. R., and Schimmel, P. R. (1980). In Biophysical Chemistry. Part II Techniques for the Study of Biological Structure and Function. W. H. Freeman and Company, San Francisco. pp. 380–381.

Cohen, S. L., and Chait, B. T. (1996). Influence of matrix solution conditions on the MALDI-MS analysis of peptides and proteins. *Anal. Chem.* 68, 31–37.

Cohen, S. L., Ferre-D'Amare, A. R., Burley, S. K., and Chait, B. T. (1995). Probing the solution structure of the DNA-binding protein Max by a combination of proteolysis and mass spectrometry. *Protein Sci.* 4, 1088–1099.

Darnell, J. E., Jr., Kerr, I. M., and Stark, G. M. (1994). Jak-STAT pathways and transcriptional activation in response to IFNs and other extracellular signaling proteins. *Science* 264, 1415–1421.

Fried, M., and Crothers, D. M. (1981). Equilibria and kinetics of lac repressor-operator interactions by polyacrylamide gel electrophoresis. *Nucl. Acids Res.* 9, 6505–6525.

Fu, X.-Y. (1992). A transcription factor with SH2 and SH3 domains is directly activated by an interferon α-induced cytoplasmic protein tyrosine kinase(s). *Cell* 70, 323–335.

Garner, M. M., and Revzin, A. (1981). A gel electrophoresis method for quantifying the binding of proteins to specific DNA regions: application to components of the *Escherichia coli* lactose operon regulatory system. *Nucl. Acids Res.* 9, 3047–3060.

Gruenwald, S., and Heitz, J. (1993). Baculovirus Expression Vector System: Procedures & Methods Manual, 2nd Ed. *PharMingen, San Diego, Calif.*

Guyer, N. B., Severns, C. W., Wong, P., Feghali, C. A., and Wright, T. M. (1995). IFN-γ induces a p91/Stat1α-related transcription factor with distinct activation and binding properties. *J. Immunol.* 155, 3472–3480.

Horvath, C. M., Wen, Z., and Darnell, J. E., Jr. (1995). A STAT protein domain that determines DNA sequence recognition suggests a novel DNA-binding domain. *Genes & Devel.* 9, 984–994.

Ihle, J. N. (1995). Cytokine receptor signalling. *Nature* 377, 591–594.

LeGendre, N., and Matsudaira, P. (1988). Direct protein microsequencing from Immobilon-P Transfer Membrane. *Biotechniques* 6, 154–159.

Leung, S., Li, X. and Stark, G. R., (1996). STATs Find That Hanging Together Can Be Stimulating. *Science* 273 750–751.

Levy, D. E., Kessler, D. S., Pine, R. I., and Darnell, J. E., Jr. (1989). Cytoplasmic activation of ISGF3, the positive regulator of interferon-α stimulated transcription, reconstituted in vitro. *Genes & Devel.* 3, 1362–1372.

Muller, M., Laxton, C., Briscoe, J., Schindler, C., Improta, T., Darnell, J. E., Jr., Stark, G. R., and Kerr, I. M. (1993). Complementation of a mutant cell line: Central role of the 91-kDa polypeptide of ISGF3 in the interferon-α and -γ signal transduction pathway. *EMBO J* 12, 4221–4228.

Quelle, F. W., Thierfelder, W., Witthuhn, B. A., Tang, B., Cohen, S., and Ihle, J. N. (1995). Phosphorylation and activation of the DNA binding activity of purified Stat1 by the Janus protein tyrosine kinases and epidermal growth factor receptor. *J. Biol. Chem.* 270, 20775–20780.

Qureshi, S. A., Salditt-Georgieff, M., and Darnell, J. E., Jr. (1995). Tyrosine phosphorylated Stat1 and Stat2 plus a 48 kD protein all contact DNA in forming the interferon stimulated gene factor 3 (ISGF3). *Proc. Natl. Acad. Sci. USA* 92, 3929–3833.

Riggs, A. D., Suzuki, H., and Bourgeois, S. (1970). lac repressor-operator interaction. I. Equilibrium studies. *J. Mol. Biol.* 48, 67–83.

Schindler, C., and Darnell, J. E., Jr. (1995). Transcriptional responses to polypeptide ligands: The JAK-STAT pathway. *Annu. Rev. Biochem.* 64, 621–51.

Schindler, C., Fu, X.-Y., Improta, T., Aebersold, R., and Darnell, J. E., Jr. (1992). Proteins of transcription factor ISGF-3: One gene encodes the 91 and 84 kDA ISGF-3 proteins that are activated by interferon-α. *Proc. Natl. Acad. Sci. USA* 89, 7836–7839.

Shuai, K., Horvath, C. M., Tsai-Huang, L. H., Qureshi, S., Cowburn, D., and Darnell, J. E., Jr. (1994). Interferon activation of the transcription factor Stat91 involves dimerization through SH2-phosphotyrosyl peptide interactions. *Cell* 76, 821–828.

Shuai, K., Schindler, C., Prezioso, V. R., and Darnell, J. E., Jr. (1992). Activation of transcription by IFN-γ: tyrosine phosphorylation of a 91 kD DNA binding protein. *Science* 259, 1808–1812.

Shuai, K., Stark, G. R., Kerr, I. M., and Darnell, J. E., Jr. (1993a). A single phosphotyrosine residue of Stat91 required for gene activation by interferon-γ. *Science* 261, 1744–1746.

Shuai, K., Ziemiecki, A., Wilks, A. F., Harpur, A. G., Sadowski, H. B., Gilman, M. Z., and Darnell, J. E., Jr. (1993b). Polypeptide signaling to the nucleus through tyrosine phosphorylation of JAK and STAT proteins. *Nature* 366, 580–583.

Stone, S. R., Hughes, M. J., and Jost, J. P. (1991). Qualitative and quantitative studies of protein-DNA interactions by gel mobility-shift assay. In Jost, J. P. & Saluz, H. P. (eds.) *A Laboratory Guide to In Vitro Studies of Protein-DNA Interactions* BioMethods, vol.5, 163–195.

Studier, F. W., and Moffatt, B. A. (1986). Use of bacteriophage T7 RNA polymerase to direct selective high-level expression of cloned genes. *J. Mol. Biol.* 189, 113–130.

Wagner, B. J., Hayes, T. E., Hoban, C. J., and Cochran, B. H. (1990). The SIF binding element confers sis/PDGF inducibility onto the c-fos promoter. *EMBO J.* 9, 4477–4484.

Wen, Z., Zhong, Z., and Darnell, J. E., Jr. (1995). Maximal activation of transcription of Stat1 and Stat3 requires both tyrosine and serine phosphorylation. *Cell* 82, 241–250.

Xu, X., Sun, Y.-L., Hoey, T. (1996). Cooperative DNA Binding and Sequence-Selective Recognition Conferred by the STAT Amino-Terminal Domain. *Science* 273, 794–797.

Yan, H., Krishnan, K., Greenlund, A. C., Gupta, S., Lim, J. T. E., Schreiber, R. D., Schindler, C. W., and Krolewski, J. J. (1996). Phosphorylated interferon-α receptor 1 subunit (IFNaR1) acts as a docking site for the latent form of the 113 kDa STAT2 protein. *EMBO J.* 15, 1064–1074.

Yan, R., Qureshi, S., Zhong, Z., Wen, Z., and Darnell, J. E., Jr. (1995). The genomic structure of the STAT genes: Multiple exons in coincident sites in Stat1 and Stat2. *Nucl. Acids Res.* 23, 459–463.

Yan, R., Small, S., Desplan, C., Dearolf, C. R., and Darnell, J., J. E. (1996). Identification of a Stat gene that functions in Drosophila development. *Cell* 84, 421–430.

Yarden, Y., Harari, I., and Schlessinger, J. (1985). Purification of an active EGF receptor kinase with monoclonal antireceptor antibodies. *J. Biol. Chem.* 260, 315–319.

The citation of any reference herein should not be construed as an admission that such reference is available as "Prior Art" to the instant application.

What is claimed is:

1. A method for identifying a drug that modulates the ability of adjacent STAT protein dimers to interact and bind to adjacent DNA binding sites comprising:
   a) measuring the binding affinity of the STAT protein, or a fragment thereof that comprises the N-terminal domain, to a nucleic acid comprising 2 adjacent weak STAT DNA binding sites in the presence and absence of a test compound;
   b) measuring the binding affinity of the STAT protein, or the fragment, to a nucleic acid comprising a single strong STAT binding site in the presence and absence of the test compound; and
   c) comparing the binding affinity measured in step (a) in the presence and absence of the test compound with the binding affinity measured in step (b) in the presence and absence of the test compound, wherein a test compound which causes an increase in the binding affinity measured in step (a) but not in the binding affinity measured in step (b) is identified as a drug that enhances the interaction between adjacent activated STAT dimers, and a test compound which causes a decrease in the binding affinity measured in step (a) but not in the binding affinity measured in step (b) is identified as a drug that inhibits the interaction between adjacent activated STAT dimers.

2. A method for identifying a drug that modulates the ability of adjacent STAT protein dimers to interact and bind to adjacent DNA binding sites comprising:
   a) measuring the binding affinity of the STAT protein, or a fragment thereof comprising the N-terminal domain, to a nucleic acid comprising 2 adjacent weak STAT DNA binding sites in the presence and absence of a test compound;
   b) measuring the binding affinity of a truncated form of the STAT protein lacking the N-terminal domain with the nucleic acid in the presence and absence of the test compound; and
   c) comparing the binding affinity measured in step (a) in the presence and absence of the test compound with the binding affinity measured in step (b) in the presence and absence of the test compound, wherein a test compound which causes an increase in the binding affinity measured in step (a) but not in the binding affinity measured in step (b) is identified as a drug that enhances the interaction between adjacent activated STAT dimers, and a test compound which causes a decrease in the binding affinity measured in step (a) but not in the binding affinity measured in step (b) is identified as a drug that inhibits the interaction between adjacent activated STAT dimers.

3. A method for identifying a drug that modulates the ability of adjacent STAT protein dimers to interact and bind to adjacent DNA binding sites comprising measuring the ability of a first STAT protein dimer fragment comprising the N-terminal domain to bind to a second STAT protein dimer fragment comprising the N-terminal domain in the presence and absence of a test compound, wherein a test compound which increases the ability of the first fragment to bind to the second fragment is identified as a drug that enhances the interaction between adjacent activated STAT dimers, and a test compound which decreases the ability of the first fragment to bind to the second fragment is identified as a drug that inhibits the interaction between adjacent activated STAT dimers.

4. The method of claim 3 wherein either said first fragment or said second fragment is labeled.

5. The method of claim 3 wherein said first fragment and said second fragment are labeled.

6. The method of claim 3 wherein said first fragment is bound to a solid support.

7. The method of claim 6 wherein said second fragment is labeled.

* * * * *